United States Patent [19]

Shinkai

[11] Patent Number: 5,728,720
[45] Date of Patent: Mar. 17, 1998

[54] ISOXAZOLIDINEDIONE COMPOUNDS AND USE THEREOF

[75] Inventor: Hisashi Shinkai, Takatsuki, Japan

[73] Assignee: Japan Tobacco Inc., Tokyo, Japan

[21] Appl. No.: 522,264

[22] PCT Filed: Dec. 26, 1994

[86] PCT No.: PCT/JP94/02233

§ 371 Date: Aug. 25, 1995

§ 102(e) Date: Aug. 25, 1995

[87] PCT Pub. No.: WO95/18125

PCT Pub. Date: Jul. 6, 1995

[30] Foreign Application Priority Data

Dec. 27, 1993 [JP] Japan .................. 5-354385

[51] Int. Cl.$^6$ .................. A61K 31/42; C07D 413/02
[52] U.S. Cl. .................. 514/374; 514/252; 514/256; 514/259; 514/314; 514/340; 544/238; 544/284; 544/333; 546/167; 546/274.1; 548/236
[58] Field of Search .................. 514/374, 380; 548/236

[56] References Cited

U.S. PATENT DOCUMENTS

| | | | |
|---|---|---|---|
| 4,572,912 | 2/1986 | Yoshioka et al. | 514/369 |
| 4,725,610 | 2/1988 | Meguro | 548/183 |
| 4,999,366 | 3/1991 | Izydore et al. | 514/380 |
| 5,391,565 | 2/1995 | Hindley et al. | 514/375 |
| 5,478,852 | 12/1995 | Olefsky et al. | 514/375 |
| 5,498,621 | 3/1996 | Dow et al. | 514/375 |

FOREIGN PATENT DOCUMENTS 3-170478  7/1991  Japan .

OTHER PUBLICATIONS

Burger, Ed. "Medicinal Chemistry 2nd Ed" Interscience, N.Y. 1960 p. 42.
Derwent Abstract of Japanese Patent Unexamined Publication JP-A-61-85372.
Derwent Abstract of Japanese Patent Unexamined Publication JP-A-60-51189.
Derwent Abstract of Japanese Patent Unexamined Publication JP-3-170478.
Derwent Abstract of WO92/02520.

*Primary Examiner*—Donald G. Daus
*Attorney, Agent, or Firm*—Wenderoth, Lind & Ponack

[57] ABSTRACT

Novel isoxazolidinedione derivatives of the formula (I)

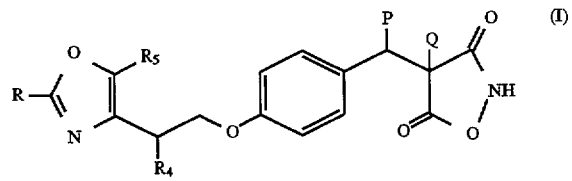

wherein R is an optionally substituted aromatic hydrocarbon, an optionally substituted alicyclic hydrocarbon, an optionally substituted heterocyclic group, an optionally substituted condensed heterocyclic group or a group of the formula

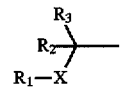

$R_4$ is a hydrogen atom, a lower alkyl or a hydroxy; $R_5$ is a lower alkyl optionally substituted by hydroxy; and P and Q are each a hydrogen atom or P and Q together form a bond, and pharmaceutically acceptable salts thereof. Said novel isoxazolidinedione derivatives and pharmaceutically acceptable salts thereof have superior hypoglycemic and hypolipidemic actions and are useful for the treatment of diabetes and the complications thereof, as well as therapeutic agents for related diseases such as hyperlipidemia.

10 Claims, No Drawings

ISOXAZOLIDINEDIONE COMPOUNDS AND USE THEREOF

BACKGROUND OF THE INVENTION

1. Field of the Invention

The present invention relates to novel isoxazolidinedione derivatives. Note particularly, the present invention relates to novel isoxazolidinedione derivatives which have hypoglycemic action and hypolipidemic action, and are useful as therapeutic agents for diabetes and the complications thereof, and as therapeutic agents for the related diseases such as hyperlipidemia.

2. Description of the Related Art

In general, the treatment of non-insulin-dependent diabetes mellitus (NIDDM) involves a combination of alimentotherapy, kinesitherapy, and administration of insulin or oral hypoglycemic agents. As the oral hypoglycemic agents, there are currently known sulfonylureas such as tolbutamide, chlorpropamide, acetohexamide, glibenclamide and tolazamide and biguanides such as phenformin, buformin and metformin.

While the sulfonylureas have strong hypoglycemic action, they sometimes induce severe and prolonged hypoglycemia, and chronic use thereof may impair their effectiveness. In addition, the biguanides frequently induce severe lactic acidosis. For these reasons, the use of these medications has required considerable attention.

Japanese Patent Unexamined Publication No. 85372/1986 corresponding to U.S. Pat. No. 4,725,610 teaches that thiazolidinedione derivatives such as [5-[4-[2-(5-methyl-2-phenyl-4-oxazolyl)ethoxy]benzyl]-2,4-thiazolidinedione] have hypoglycemic action, and Japanese Patent Unexamined Publication No. 51189/1985 corresponding to U.S. Pat. No. 4,572,912 teaches that thiazolidinedione derivatives such as [(±)-5-[4-(6-hydroxy-2,5,7,8-tetramethylchroman-2-yl-methoxy)benzyl]-2,4-thiazolidinedione] have hypoglycemic action. It has been also taught that oxazolidinedione derivatives such as [5-[4-[2-(2-phenyl-5-methyloxazol-4-yl)ethoxy]benzyl]-2,4-oxazolidinedione] described in Japanese Patent Unexamined Publication No. 170478/1991 corresponding to U.S. Pat. No. 5,498,621 and [5-[4-[2-[N-(2-benzoxazolyl)-N-methyl]aminoethoxy]benzyl]-2,4-oxazolidinedione] described in WO92/02520 corresponding to U.S. Pat. No. 5,391,565 possess hypoglycemic action and cholesterol lowering action.

However, these compounds are not necessarily satisfactory in terms of activity, and the use thereof rather causes anxiety when their side effects (e.g. toxicity) are taken into consideration. These publications do not include a description suggesting an isoxazolidinedione derivative such as the compounds of the present invention.

SUMMARY OF THE INVENTION

The present inventors have conducted intensive studies in an effort to provide a compound effective as a therapeutic drug for diabetes, the complications thereof and hyperlipidemia, and found novel low toxic isoxazolidinedione derivatives having superior hypoglycemic action and hypolipidemic action, which resulted in the completion of the invention.

Accordingly, the present invention relates to novel isoxazolidinedione derivatives of the following (1) to (14).

(1) Novel isoxazolidinedione derivatives of the formula (I)

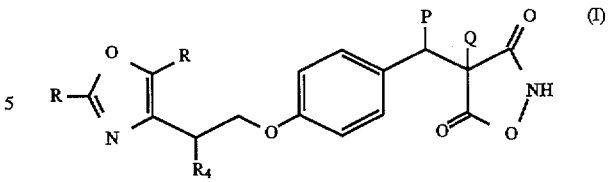

wherein

R is an optionally substituted aromatic hydrocarbon, an optionally substituted alicyclic hydrocarbon, an optionally substituted heterocyclic group, an optionally substituted condensed heterocyclic group or a group of the formula

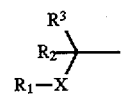

wherein $R_1$ is an optionally substituted aromatic hydrocarbon, an optionally substituted alicyclic hydrocarbon, an optionally substituted heterocyclic group or an optionally substituted condensed heterocyclic group, $R_2$ and $R_3$ are the same or different and each is a hydrogen atom or a lower alkyl, and X is an oxygen atom, a sulfur atom or a secondary amino;

$R_4$ is a hydrogen atom, a lower alkyl or a hydroxy;

$R_5$ is a lower alkyl optionally substituted by hydroxy; and

P and Q are each a hydrogen atom or P and Q together form a bond, and pharmaceutically acceptable salts thereof.

(2) The novel isoxazolidinedione derivatives of the above (1) wherein $R_4$ is a hydrogen atom and $R_5$ is a lower alkyl, and pharmaceutically acceptable salts thereof.

(3) The novel isoxazolidinedione derivatives of the above (2) wherein R is an optionally substituted phenyl, an optionally substituted 5- or 6-membered aromatic heterocyclic group having 1 or 2 hetero atoms selected from sulfur atom, oxygen atom and nitrogen atom, or an optionally substituted condensed aromatic heterocyclic group wherein such aromatic heterocyclic ring and a benzene ring are condensed, and pharmaceutically acceptable salts thereof.

(4) The novel isoxazolidinedione derivatives of the above (3) wherein R is a phenyl, a 5- or 6-membered aromatic heterocyclic group having one or two hetero atoms selected from sulfur atom, oxygen atom and nitrogen atom, or a condensed aromatic heterocyclic group wherein such aromatic heterocyclic ring and a benzene ring are condensed, and pharmaceutically acceptable salts thereof.

(5) The novel isoxazolidinedione derivatives of the above (3) wherein R is a phenyl, or a condensed aromatic heterocyclic group wherein a benzene ring and a 5- or 6-membered heterocyclic group having sulfur atom are condensed, and pharmaceutically acceptable salts thereof.

(6) The novel isoxazolidinedione derivatives of the above (2) wherein R is a phenyl, a benzothienyl or 1-methyl-1-(2-pyridylthio)methyl, and pharmaceutically acceptable salts thereof.

(7) The novel isoxazolidinedione derivatives of the above (2) wherein R is a phenyl, and pharmaceutically acceptable salts thereof.

(8) The novel isoxazolidinedione derivatives of the above (2) wherein R is a group of the formula

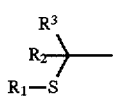

and pharmaceutically acceptable salts thereof.

(9) The novel isoxazolidinedione derivatives of the above (8) wherein $R_1$ is an optionally substituted phenyl or an optionally substituted 5- or 6-membered aromatic heterocyclic group having one or two hetero atoms selected from sulfur atom, oxygen atom and nitrogen atom, and pharmaceutically acceptable salts thereof.

(10) The novel isoxazolidinedione derivatives of the above (8) wherein $R_1$ is a 5- or 6-membered aromatic heterocyclic group having one or two hetero atoms selected from sulfur atom, oxygen atom and nitrogen atom, and pharmaceutically acceptable salts thereof.

(11) The novel isoxazolidinedione derivatives of the above (8) wherein $R_1$ is a 5- or 6-membered aromatic heterocyclic group having nitrogen atom, and pharmaceutically acceptable salts thereof.

(12) The novel isoxazolidinedione derivatives of the above (8) wherein $R_1$ is pyridyl, and pharmaceutically acceptable salts thereof.

(13) The novel isoxazolidinedione derivative of the above (1) which is selected from the group of
4-[4-[2-(2-phenyl-5-methyl-4-oxazolyl)ethoxy]benzyl]-3,5-isoxazolidinedione;
4-[4-[2-(2-phenyl-5-methyl-4-oxazolyl)ethoxy]benzylidene]-3,5-isoxazolidinedione;
4-[4-[2-(2-benzothienyl-5-methyl-4-oxazolyl)ethoxy]benzyl]-3,5-isoxazolidinedione; and
4-[4-[2-[5-methyl-[2-(2-pyridylthio)ethyl]-4-oxazolyl]ethoxy]benzyl]-3,5-isoxazolidinedione;
and pharmaceutically acceptable salts thereof.

(14) Pharmaceutical compositions comprising the novel isoxazolidinedione derivative of the above (1) or a pharmaceutically acceptable salt thereof, and a carrier.

(15) Pharmaceutical compositions of the above (14) which are agents for the prevention and treatment of diabetes.

(16) Pharmaceutical compositions of the above (14) which are agents for the prevention and treatment of hyperlipidemia.

(17) Pharmaceutical compositions of the above (14) which are agents for preventing arteriosclerosis.

As used here in the present specification, "aromatic hydrocarbon" means phenyl, biphenyl, naphthyl and the like. It may be aralkyl such as benzyl, with preference given to phenyl.

"Alicyclic hydrocarbon" means that having 3 to 7 carbon atoms, and is exemplified by cyclopropyl, cyclobutyl, cyclopentyl, cyclohexyl, cycloheptyl, cyclopropenyl, cyclobutenyl, cyclobutadienyl, cyclopentenyl, cyclopentadienyl, cyclohexenyl, cyclohexadienyl, cycloheptenyl and cycloheptadienyl. Preferred is alicyclic hydrocarbon having 5 to 7 carbon atoms, such as cyclopentyl, cyclohexyl, cycloheptyl, cyclopentenyl, cyclopentadienyl, cyclohexenyl, cyclohexadienyl, cycloheptenyl and cycloheptadienyl, with preference given to cyclopentyl and cyclohexyl.

"Heterocyclic group" is a 5- or 6-membered heterocyclic group, preferably aromatic heterocyclic group having, as an atom constituting the ring besides carbon atom, 1 to 3, preferably 1 or 2, hetero atoms selected from nitrogen atom, oxygen atom and sulfur atom. Specific examples include thienyl, furyl, pyrrolyl, imidazolyl, pyrazolyl, thiazolyl, isothiazolyl, oxazolyl, isoxazolyl, oxadiazolyl, thiadiazolyl, triazolyl, pyridyl, pyrazinyl, pyrimidinyl, pyridazinyl, triazinyl, dithiazolyl, dioxolanyl, dithiolyl, pyrrolidinyl, dithiadiazinyl, thiadiazinyl, morpholinyl, oxazinyl, thiazinyl, piperazinyl, pyperidinyl, pyranyl and thiopyranyl, with preference given to thienyl, furyl, pyrrolyl, imidazolyl, pyridyl and pyrimidinyl, and particular preference given to pyridyl, pyrimidinyl and imidazolyl.

"Condensed heterocyclic group" means a ring wherein 5- or 6-membered heterocyclic groups, preferably aromatic heterocyclic groups having, as an atom constituting the ring besides carbon atom, 1 to 3, preferably 1 or 2, hetero atoms selected from nitrogen atom, oxygen atom and sulfur atom have been condensed, or a ring wherein such heterocyclic group, preferably aromatic heterocyclic group and a 4- to 6-membered aromatic hydrocarbon ring, preferably phenyl, have been condensed. Specific examples include furoisoxazolyl, imidazothiazolyl, thienoisothiazolyl, thienothiazolyl, thienothiazolyl, imidazopyrazolyl, cyclopentapyrazolyl, pyrrolopyrrolyl, cyclopentathienyl, thienothienyl, oxadiazolopyrazinyl, benzofurazanyl, thiadiazolopyridinyl, triazolothiazinyl, triazolopyrimidinyl, triazolopyridinyl, benzotriazolyl, oxazolopyrimidinyl, oxazolopyridinyl, benzoxazolyl, thiazolopyridazinyl, thiazolopyrimidinyl, benzoisothiazolyl, benzothiazolyl, pyrazolotriazinyl, pyrazolothiazinyl, imidazopyrazinyl, purinyl, pyrazolopyridazinyl, pyrazolopyriminidyl, imidazopyridinyl, pyranopyrazolyl, benzimidazolyl, indazolyl, benzoxathiolyl, benzodioxalyl, dithioropyrimidinyl, benzodithiolyl, indolidinyl, indolyl, isoindolyl, furopyrimidinyl, furopyridinyl, benzofuranyl, isobenzofuranyl, thienopyrazinyl, thienopyrimidinyl, thienodioxynyl, thienopyridinyl, benzothienyl, isobenzothienyl, cyclopentaoxazinyl, cyclopentafuranyl, benzothiadiazinyl, benzotriazinyl, pyridoxazinyl, benzoxazinyl, pyrimidothiazinyl, benzothiazinyl, pyrimidopyridazinyl, pyrimidopyrimidinyl, pyridopyridazinyl, pyridopyrimidinyl, cinnolinyl, quinazolinyl, quinoxalinyl, benzoxathiinyl, benzodioxynyl, benzodithiinyl, naphthylidinyl, isoquinolinyl, quinolinyl, benzopyranyl, benzothiopyranyl, chromanyl, isochromanyl and indolinyl, with preference given to benzoxazolyl, benzoisothiazolyl, benzothiazolyl, benzimidazolyl, indazolyl, benzoxathiolyl, benzodioxalyl, benzodithiolyl, indolyl, isoindolyl, benzofuranyl, isobenzofuranyl, benzothienyl, isobenzothienyl, benzothiadiazinyl, benzotriazinyl, benzoxazinyl, benzothiazinyl, cinnolinyl, quinazolinyl, quinoxalinyl, benzoxathiinyl, benzodioxynyl, benzodithiinyl, isoquinolinyl, quinolinyl, benzopyranyl, benzothiopyranyl, chromanyl, isochromanyl and indolinyl, and particular preference given to indolyl, isoindolyl, benzofuranyl, isobenzofuranyl, benzothienyl, isobenzothienyl, isoquinolinyl and quinolinyl.

"Lower" means that the number of the carbon atoms constituting the group is 1 to 6, preferably 1 to 4.

"Lower alkyl" means alkyl having 1 to 6 carbon atoms, such as methyl, ethyl, propyl, isopropyl, butyl, isobutyl, sec-butyl, tert-butyl, pentyl, isopentyl, neopentyl, tert-pentyl, hexyl, isohexyl and neohexyl. Preferred is alkyl having 1 to 4 carbon atoms such as methyl, ethyl, propyl, isopropyl, butyl, isobutyl, sec-butyl and tert-butyl, with particular preference given to methyl.

"Optionally substituted" means that the group may be substituted by 1 to 3 same or different substituents. Examples of the substituent include lower alkyl such as methyl, ethyl, propyl, butyl and tert-butyl; lower alkoxy such as methoxy, ethoxy, propoxy, butoxy and tert-butoxy; halogen atom; nitro; cyano; hydroxy; acyl such as formyl, acetyl, propionyl, butyryl, isobutyryl, benzoyl and naphthoyl; acyloxy such as formyloxy, acetyloxy, propionyloxy, butyryloxy, isobutyryloxy and benzoyloxy; aralkyloxy such as benzyloxy, phenetyloxy and phenylpropyloxy; mercapto; alkylthio such as methylthio, ethylthio, propylthio, butoxythio, isobutoxythio and tert-butoxythio; amino; alkylamino such as methylamino, ethylamino, propylamino, isopropylamino and butylamino; dialkylamino such as dimethylamino, diethylamino, dipropylamino, diisopropylamino and dibutylamino; alkoxycarbonyl such as methoxycarbonyl, ethoxycarbonyl, propoxycarbonyl, isopropoxycarbonyl, butoxycarbonyl and tert-butoxycarbonyl; amide; trifluoromethyl; phospholyl; sulfonyl; sulfonyloxy; sulfamoyl; alkylphosphonamide such as methylphosphonamide, ethylphosphonamide, propylphosphonamide and isopropylphosphonamide; methylenedioxy; alkoxyphosphoryl such as methoxyphosphoryl, ethoxyphosphoryl, propoxyphosphoryl and isopropoxyphosphoryl; alkylsulfonyl such as methylsulfonyl, ethylsulfonyl, propylsulfonyl, butylsulfonyl and tert-butylsulfonyl; and alkylsulfonylamino such as methylsulfonylamino, ethylsulfonylamino, propylsulfonylamino, butylsulfonylamino and tert-butylsulfonylamino. Preferred are hydroxy, lower alkyl, lower alkoxy, aralkyloxy, mercapto, lower alkylthio, nitro, halogen atom, trifluoromethyl, amino, dialkylamino, alkylamino, acyl, cyano, carbamoyl, acyloxy, sulfonyl, carboxyl and alkoxycarbonyl, with particular preference given to hydroxy, lower alkyl and lower alkoxy.

"Pharmaceutically acceptable salt" may be any as long as it forms a non-toxic salt with a novel isoxazolidinedione derivative of the above-mentioned formula (I). Examples thereof include alkali metal salts such as sodium salt and potassium salt; alkaline earth metal salts such as magnesium salt and calcium salt; ammonium salt; organic base salts such as trimethylamine salt, triethylamine salt, pyridine salt, pycoline salt, dicyclohexylamine salt and N,N'-dibenzylethylenediamine salt; and amino acid salts such as lysine salt and arginine salt.

The compound of the present invention has superior hypoglycemic action and hypolipidemic action, and is not only useful as an agent for the prevention and treatment of diabetes and hyperlipidemia, but also expected to be useful as an agent for preventing arteriosclerosis. When the compound of the formula (I), which is the compound of the present invention, or a pharmaceutically acceptable salt thereof is used as a pharmaceutical preparation, it is generally admixed with a pharmacologically acceptable carrier, excipient, diluent, extender, disintegrant, stabilizer, preservative, buffer, emulsifier, aromatic, coloring, sweetener, thickener, flavor, solubilizer, and other additives known per se, such as water, vegetable oil, alcohol such as ethanol and benzyl alcohol, carbohydrate such as polyethylene glycol, glycerol triacetate, gelatin, lactose and starch, magnesium stearate, talc, lanolin, petrolatum and the like, and formulated into tablet, pill, powder, granule, suppository, injection, eye drop, liquid, capsule, troche, aerosol, elixir, suspension, emulsion, syrup and the like which may be administered orally or parenterally. While the dose varies depending on the kind and severity of the disease, the compound to be administered, administration route, age, sex and body weight of patient and the like, the compound (I) is preferably administered orally at a dose of, in general, 0.01–1,000 mg, particularly 0.05–100 mg per day to an adult.

The compound of the formula (I) has one or more asymmetric carbons. When it has one asymmetric carbon, a pure optically active compound, a mixture thereof at an optional proportion or a racemate exists; and when it has two or more asymmetric carbons, optically pure diastereomers, racemates thereof, a combination of these or a mixture thereof at an optional proportion exist(s). These are all encompassed in the present invention. Depending on the case, they may be hydrates. As is evident from the structure, the above-mentioned compound (I) can exist as a keto-enol type tautomer, which is also within the scope of the present invention.

The compound of the present invention can be synthesized, for example, by the following methods. It is needless to say that the production method of the compound of the present invention is not limited to them.

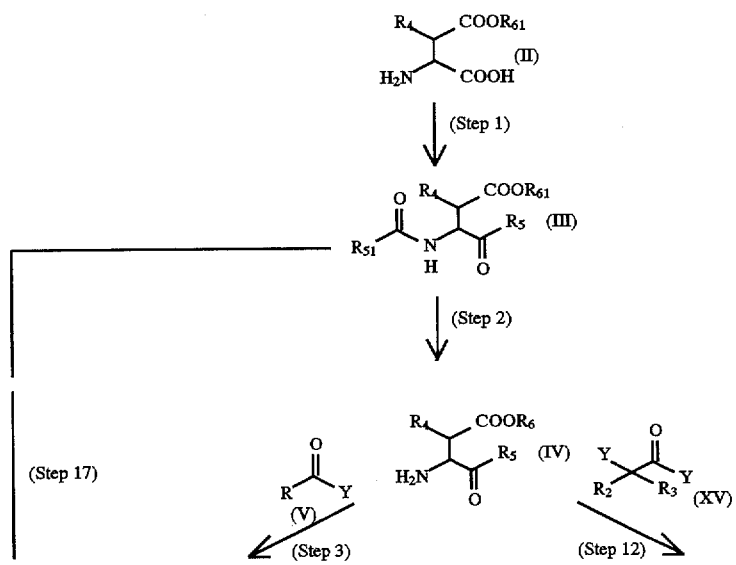

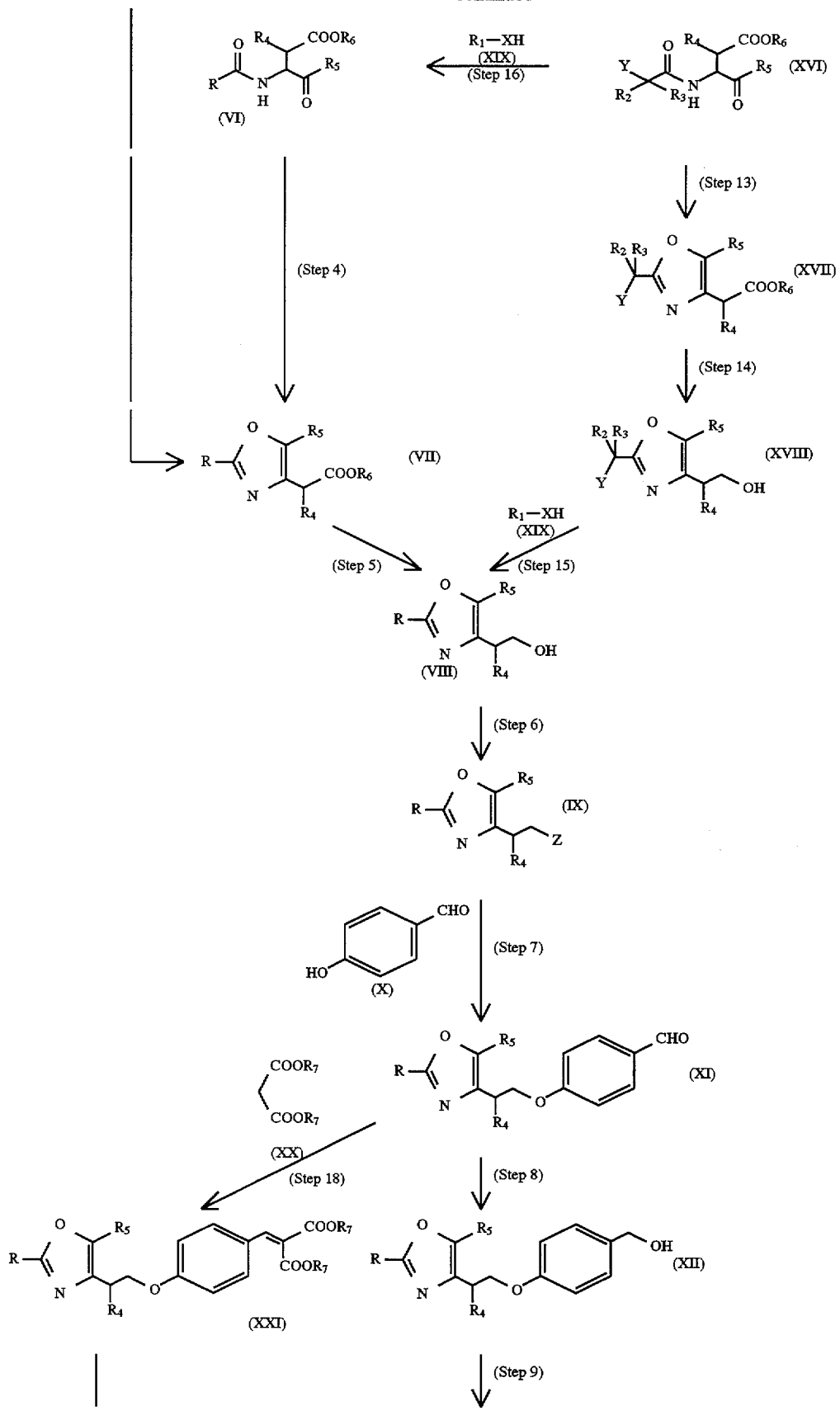

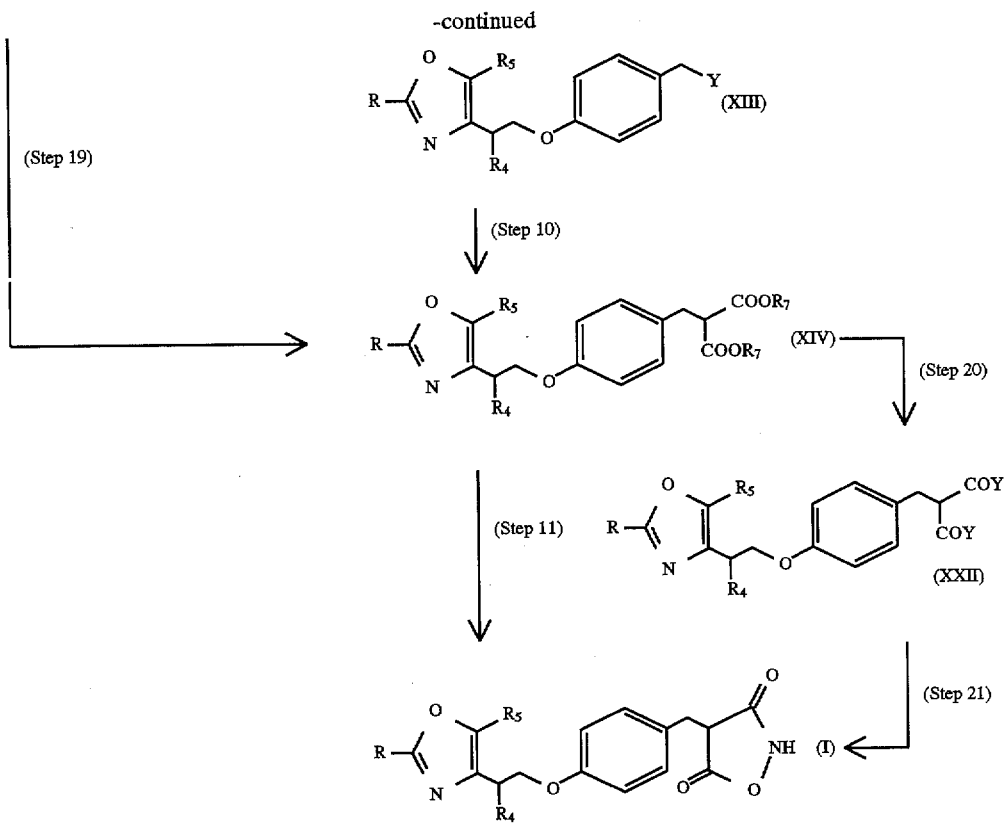

DETAILED DESCRIPTION OF THE PREFERRED EMBODIMENTS

Step 1

The compound (III) wherein $R_{61}$ is a carboxy-protecting group such as benzyl, $R_{51}$ is a lower alkyl, an optionally substituted aromatic hydrocarbon, an optionally substituted alicyclic hydrocarbon, an optionally substituted heterocyclic group, an optionally substituted condensed heterocyclic group or a group of the formula

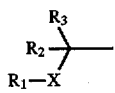

wherein $R_1$, $R_2$ and $R_3$ are as defined above, and $R_4$ and $R_5$ are as defined above, can be synthesized by reacting compound (II) wherein $R_4$ and $R_{61}$ are as defined above, which is an aspartate derivative, in the presence of pyridine or a base such as triethylamine, in acid anhydride such as acetic anhydride and propionic anhydride, at room temperature to heating, and treating the resulting compound with water. In this reaction, addition of 4-dimethylaminopyridine sometimes affords better results.

Step 2

The compound (IV) wherein $R_6$ is an alkyl, and $R_4$ and $R_5$ are as defined above, is obtained by removing N-acyl such as N-acetyl of the formula $R_{51}$—CO— by heating compound (III) wherein $R_4$, $R_5$, $R_{51}$ and $R_{61}$ are as defined above, in an acidic solvent such as hydrochloric acid. Since $R_6$ is eliminated at the same time, the resulting compound is esterified by reacting same in an alcohol solvent such as methanol, ethanol and propanol, in the presence of an acid such as hydrogen chloride, whereby compound (IV) is obtained.

Step 3

The compound (VI) wherein R, $R_4$, $R_5$ and $R_6$ are as defined above, can be synthesized by reacting compound (IV) wherein $R_4$, $R_5$ and $R_6$ are as defined above, and compound (V) wherein Y is a halogen atom and R is as defined above, in an organic solvent such as benzene, toluene, dichloromethane, chloroform, ether, dioxane, tetrahydrofuran, acetonitrile, dimethoxyethane, pyridine and acetone or a mixed solvent thereof, in the presence of a base such as triethylamine, pyridine and N-methylmorpholine under cooling to room temperature.

Step 4

The compound (VII) wherein R, $R_4$, $R_5$ and $R_6$ are as defined above, can be synthesized by reacting compound (VI) wherein R, $R_4$, $R_5$ and $R_6$ are as defined above, in an organic solvent such as benzene, toluene, acetonitrile, chloroform and tetrahydrofuran, or without solvent, in the presence of an acid catalyst such as sulfuric acid and p-toluenesulfonic acid and a dehydrating agent such as acetic anhydride, at room temperature to under heating, preferably under heating.

Step 5

The compound (VIII) wherein R, $R_4$ and $R_5$ are as defined above, can be synthesized by reducing compound (VII) wherein R, $R_4$, $R_5$ and $R_6$ are as defined above, by a conventional method, using a reducing agent such as diisobutyl aluminum hydride, in an organic solvent such as benzene, toluene, ether, dioxane and tetrahydrofuran.

Step 6

The compound (IX) wherein Z is p-toluenesulfonyloxy, benzenesulfonyloxy, methanesulfonyloxy or a leaving group such as halogen atom and the like, and R, $R_4$ and $R_5$ are as defined above, can be synthesized by reacting compound (VIII) wherein R, $R_4$ and $R_5$ are as defined above, and sulfonyl chloride such as p-toluenesulfonyl chloride, benzenesulfonyl chloride and methanesulfonyl chloride, or a halogenating agent such as phosphorus tribromide and thionyl chloride, in an organic solvent such as benzene, toluene, dichloromethane, chloroform, ether, dioxane, tetrahydrofuran, acetonitrile, dimethylformamide, dimethylsulfoxide, acetone and ethyl acetate, or a mixed solvent thereof, or without solvent, in the presence of a base such as triethylamine, 4-dimethylaminopyridine and pyridine, under cooling to under heating.

Step 7

The compound (XI) wherein R, $R_4$ and $R_5$ are as defined above, can be synthesized by reacting compound (IX) wherein R, $R_4$, $R_5$ and Z are as defined above, and 4-hydroxybenzaldehyde (X) in an organic solvent such as benzene, toluene, dichloromethane, chloroform, ether, dioxane, tetrahydrofuran, acetonitrile, dimethylformamide, dimethylsulfoxide, sulforan and dimethoxyethane, in the presence of a base such as sodium hydride, potassium hydride, sodium amide, sodium alkoxide, potassium alkoxide, triethylamine and sodium hydroxide, under cooling to under heating.

Step 8

The compound (XII) wherein R, $R_4$ and $R_5$ are as defined above can be synthesized by reducing compound (XI) wherein R, $R_4$ and $R_5$ are as defined above, using a catalyst such as sodium borohydride, lithium aluminum hydride, lithium borohydride and dibutyl aluminum hydride, in a solvent such as ethanol and isopropanol.

Step 9

The compound (XIII) wherein R, $R_4$, $R_5$ and Y are as defined above, can be synthesized by reacting compound (XII) wherein R, $R_4$ and $R_5$ are as defined above, in a solvent such as pyridine and dioxane in the presence or absence of a catalyst such as zinc chloride, adding a halogenating agent such as hydrogen bromide, phosphorus trichloride, phosphorus tribromide and thionyl chloride, at room temperature to under heating. It can be also synthesized by reacting compound (XII) wherein R, $R_4$ and $R_5$ are as defined above, in a solvent such as anhydrous carbon tetrachloride, adding triphenylphosphine, at room temperature to under heating.

Step 10

The compound (XIV) wherein $R_7$ is a lower alkyl, and R, $R_4$ and $R_5$ are as defined above, can be synthesized by reacting compound (XIII) wherein R, $R_4$, $R_5$ and Y are as defined above, with malonic diester, in an organic solvent such as benzene, toluene, dichloromethane, chloroform, ether, dioxane, tetrahydrofuran, acetonitrile, dimethylformamide, dimethylsulfoxide, sulforan and dimethoxyethane, in the presence of a base such as sodium hydride, potassium hydride, sodium amide, sodium alkoxide, potassium alkoxide, triethylamine and sodium hydroxide, under cooling to under heating.

Step 11

The compound (I) wherein R, $R_4$ and $R_5$ are as defined above, can be synthesized by reacting compound (XIV) wherein R, $R_4$, $R_5$ and $R_7$ are as defined above, with hydroxyamine in an anhydrous alcohol solution, under cooling to under heating.

When the compound has hydroxy as the substituent for R, a compound having methoxy and the like as the substituent is synthesized and hydrolyzed under acidic conditions.

The compound (VIII) can be synthesized by introducing substituent $R_1$ after ring closure, as mentioned below.

Step 12

The compound (XVI) wherein $R_2$, $R_3$, $R_4$, $R_5$, $R_6$ and Y are as defined above, can be synthesized by reacting compound (IV) wherein $R_4$, $R_5$ and $R_6$ are as defined above, with compound (XV) wherein $R_2$, $R_3$ and Y are as defined above, in an organic solvent such as benzene, toluene, dichloromethane, chloroform, ether, dioxane, tetrahydrofuran, acetonitrile, dimethoxyethane, pyridine and acetone, or a mixed solvent thereof, in the presence of a base such as triethylamine, pyridine and N-methylmorpholine, under cooling to room temperature.

Step 13

The compound (XVII) wherein $R_2$, $R_3$, $R_4$, $R_5$, $R_6$ and Y are as defined above, can be synthesized by reacting compound (XVI) wherein $R_2$, $R_3$, $R_4$, $R_5$, $R_6$ and Y are as defined above, in an organic solvent such as benzene, toluene, acetonitrile, chloroform and tetrahydrofuran or without solvent, in the presence of an acid catalyst such as sulfuric acid and p-toluenesulfonic acid and a dehydrating agent such as acetic anhydride, at room temperature to under heating, preferably under heating.

Step 14

The compound (XVIII) wherein $R_2$, $R_3$, $R_4$, $R_5$ and Y are as defined above, can be synthesized by reducing compound (XVII) wherein $R_2$, $R_3$, $R_4$, $R_5$ and Y are as defined above, in an organic solvent such as benzene, toluene, ether, dioxane and tetrahydrofuran, using a reducing agent such as diisobutyl aluminum hydride, by a conventional method.

Step 15

The compound (VIII) wherein R, $R_4$ and $R_5$ are as defined above, can be synthesized by reacting compound (XVIII) wherein $R_2$, $R_3$, $R_4$, $R_5$ and Y are as defined above, and compound (XIX) wherein $R_1$ and X are as defined above, in an organic solvent such as benzene, toluene, dichloromethane, chloroform, ether, dioxane, tetrahydrofuran, acetonitrile, dimethylformamide and dimethylsulfoxide, water or a mixed solvent thereof, in the presence of a base such as sodium hydride, potassium hydride, sodium amide, sodium alkoxide, potassium alkoxide, triethylamine and sodium hydroxide, under cooling to under heating.

The compound (VI) can be also synthesized by the following steps.

Step 16

The compound (VI) wherein R, $R_4$, $R_5$ and $R_6$ are as defined above, can be synthesized by reacting compound (XVI) wherein $R_2$, $R_3$, $R_4$, $R_5$, $R_6$ and Y are as defined above, and compound (XIX) wherein $R_1$ and X are as defined above, in an organic solvent such as benzene, toluene, dichloromethane, chloroform, ether, dioxane, tetrahydrofuran, acetonitrile, dimethylformamide and dimethylsulfoxide, water or a mixed solvent thereof, in the presence of a base such as sodium hydride, potassium hydride, sodium amide, sodium alkoxide, potassium alkoxide, triethylamine and sodium hydroxide, under cooling to under heating.

Step 17

The compound (VII) wherein R, $R_4$, $R_5$ and $R_6$ are as defined above, can be synthesized by reacting compound (III) wherein $R_4$, $R_5$, $R_{51}$ and $R_{61}$ are as defined above, in an organic solvent such as benzene, toluene, acetonitrile, chloroform and tetrahydrofuran or without solvent, in the presence of an acid catalyst such as sulfuric acid and p-toluenesulfonic acid and a dehydrating agent such as acetic anhydride, at room temperature to under heating, preferably under heating.

Step 18

The compound (XXI) wherein R, $R_4$, $R_5$ and $R_7$ are as defined above, can be synthesized by refluxing under heating compound (XI) wherein R, $R_4$ and $R_5$ are as defined above, and compound (XX) wherein $R_7$ is as defined above, in an organic solvent such as toluene and benzene, using a catalyst such as piperidinium acetate, ethylene diammonium acetate and ammonium acetate, which has been formed from acetic acid and piperidine in the system, while removing water out from the system.

Step 19

The compound (XIV) wherein R, $R_4$, $R_5$ and $R_7$ are as defined above can be synthesized by reacting compound (XXI) wherein R, $R_4$, $R_5$ and $R_7$ are as defined above, in an organic solvent such as methanol, ethanol, propanol, isopropanol, tetrahydrofuran, dioxane, dichloromethane and acetic acid or a mixed solvent thereof, using a catalyst such as palladium carbon and palladium black under a hydrogen atmosphere at normal temperature to under heating.

Step 20

The compound (XXII) wherein R, $R_4$, $R_5$ and Y are as defined above, can be synthesized by hydrolyzing compound (XIV) wherein R, $R_4$, $R_5$ and $R_7$ are as defined above, to give a dicarboxylic acid and treating same with a halogenating reagent such as thionyl chloride and oxalyl chloride.

Step 21

The compound (I') wherein R, $R_4$ and $R_5$ are as defined above can be synthesized by reacting compound (XXII) wherein R, $R_4$, $R_5$ and Y are as defined above, with hydroxyl amine, in the presence of a base such as pyridine and triethylamine.

The above-mentioned methods are particularly advantageous when P and Q are hydrogen atoms.

The compound (I) thus obtained can be isolated and purified by known separation-purification means such as concentration, concentration under reduced pressure, solvent extraction, precipitation, recrystallization and chromatography.

Of the compounds (I), a compound wherein P and Q are combined, which is represented by the formula (I')

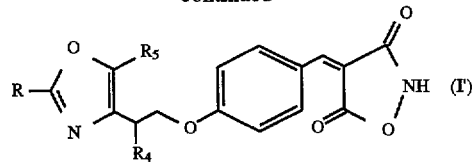

wherein R, $R_4$ and $R_5$ are as defined above, can be synthesized by, for example, the following method.

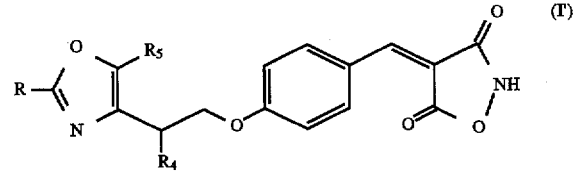

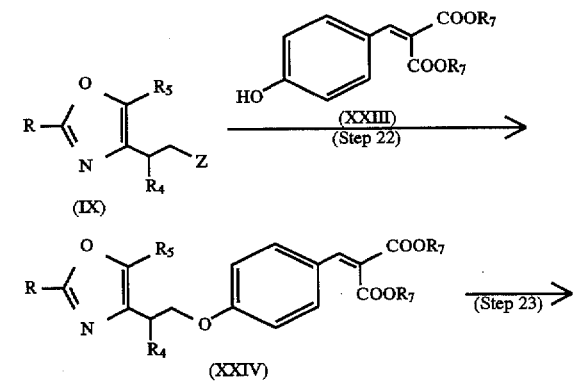

Step 22

The compound (XXI) wherein R, $R_4$, $R_5$ and $R_7$ are as defined above, can be synthesized by reacting compound (IX) wherein R, $R_4$, $R_5$ and Z are as defined above, with compound (XX) wherein $R_7$ is as defined above, in an organic solvent such as benzene, toluene, dichloromethane, chloroform, ether, dioxane, tetrahydrofuran, acetonitrile, dimethylformamide, dimethylsulfoxide, sulforan and dimethoxyethane, in the presence of a base such as sodium hydride, potassium hydride, sodium amide, sodium alkoxide, potassium alkoxide, triethylamine and sodium hydroxide, under cooling to under heating.

Step 23

The compound (I') wherein R, $R_4$ and $R_5$ are as defined above, can be synthesized by reacting compound (XXI) wherein R, $R_4$, $R_5$ and $R_7$ are as defined above, with hydroxyamine using sodium methoxide in an anhydrous methanol solution, under cooling to under heating.

The present invention is explained in more detail by way of Examples in the following, to which the present invention is not limited.

EXAMPLE 1

Step 1:

Synthesis of benzyl 3-acetamido-4-oxopentanoate

β-Benzyl L-aspartate (400 g, 1.79 mol) was suspended in triethylamine (748 ml, 5.37 mol) and acetic anhydride (676 ml, 7.16 mol) was dropwise added at 0° C. with stirring. After stirring for 30 minutes, 4-dimethylaminopyridine (20.0 g, 0.16 mol) was portionwise added under ice-cooling. The mixture was stirred overnight at room temperature, and ice was added under ice-cooling. At the end of the exothermic process, water (700 ml) was added. A 7.5N aqueous solution of potassium hydroxide was portionwise added to make its pH 9. The mixture was extracted three times with ethyl acetate (1,000 ml), and the organic layer was washed twice with 1N hydrochloric acid (1,000 ml), twice with a saturated aqueous solution of sodium hydrogencarbonate (500 ml) and with saturated brine (500 ml) in order. The layer was dried over magnesium sulfate and concentrated to dryness to give 390 g of the title compound.

Step 2:

Synthesis of methyl 3-amino-4-oxopentanoate hydrochloride

6N Hydrochloric acid (700 ml) was added to the compound (390 g, 1.50 mol) synthesized in the above Step 1, and the mixture was stirred under reflux for 2 hours. The mixture was cooled to room temperature and the reaction mixture was washed twice with dichloromethane (500 ml). The aqueous layer was concentrated to dryness. A solution of hydrogen chloride in methanol (1,500 ml) was added under ice-cooling and the mixture was stirred. The mixture was gradually warmed and the mixture was stirred overnight at room temperature. Concentration to dryness gave 247 g of a crude product. The crude product (60 g) was recrystallized from isopropanol to give 30 g of the title compound as a white solid.

Step 3:

Synthesis of methyl 3-(benzene-2-carboxamide)-4-oxopentanoate

The compound (9.40 g, 51.3 mmol) synthesized in the above Step 2 was suspended in dichloromethane (200 ml) at 0° C. Benzoyl chloride was added thereto, and N-methylmorpholine (20.8 g, 0.2 mol) was dropwise added gradually with stirring. The mixture was stirred for 3.5 hours, and water (100 ml) was added to separate an organic layer. Further, an organic layer was extracted from the aqueous layer with dichloromethane (100 ml). The extracted organic layers were combined, washed with 1N aqueous hydrochloric acid (100 ml) and water (100 ml) in order, and dried over magnesium sulfate. Concentration to dryness gave 12.75 g of the title compound (yield 100%).

Step 4:

Synthesis of methyl [2-(2-phenyl)-5-methyl-4-oxazolyl]acetate

Anhydrous acetate (70 ml) was added to the compound (12.75 g, 51.2 mmol) synthesized in the above Step 3 and the compound was dissolved. Con. sulfuric acid (1.0 ml) was dropwise added with stirring. The mixture was stirred at 90° C. for 3 hours and cooled to room temperature. Water (100 ml) was added to the reaction mixture, and the mixture was neutralized with a saturated aqueous solution of sodium hydrogencarbonate, and extracted with dichloromethane (100 ml). The extract was dried over magnesium sulfate, and concentrated to dryness to give 8.75 g of the title compound (yield 74%).

Step 5:

Synthesis of 2-[2-(2-phenyl)-5-methyl-4-oxazolyl]ethanol

A solution of the compound (8.75 g, 37.88 mmol) synthesized in the above Step 4 in toluene (200 ml) was dropwise added to a solution (133 ml, 133.20 mmol) of diisobutyl aluminum hydride in toluene at 0° C. under a nitrogen stream. Two hours later, methanol (100 ml) was dropwise added. Then, 2N hydrochloric acid (700 ml) was added to this gel reaction mixture to dissolve same, and the mixture was extracted 4 times with ethyl acetate (500 ml). The extracted organic layers were combined, washed with saturated brine (200 ml) and dried over magnesium sulfate. Concentration to dryness gave 7.69 g of the title compound (yield 100%).

Step 6:

Synthesis of 2-[2-(2-phenyl)-5-methyl-4-oxazolyl]-1-ethyltosylate

Pyridine (30 ml) was added to a solution (15 ml) of the compound (7.69 g, 37.88 mmol) synthesized in the above Step 5 in dichloromethane, and p-toluenesulfonyl chloride (7.58 g, 39.77 mmol) was gradually added at 0° C. After stirring for 6 hours, dichloromethane (100 ml) was added to dilute same, and dilute hydrochloric acid (100 ml) was added. The mixture was partitioned, and the organic layer was sequentially washed with water (100 ml), a saturated aqueous solution of sodium hydrogencarbonate (100 ml) and saturated brine (100 ml). Drying over magnesium sulfate and concentration to dryness gave 11.63 g of the title compound (yield 86%).

Step 7:

Synthesis of 4-[2-[2-(2-phenyl)-5-methyl-4-oxazolyl]ethoxy]benzaldehyde

A 60% oil of sodium hydride (3.14 g, 78.4 mmol) was washed twice with n-hexane (20 ml) under a nitrogen stream and added with dimethylformamide (20 ml), and the mixture was cooled to 0° C. A solution (20 ml) of 4-hydroxyaldehyde (9.57 g, 78.4 mmol) in dimethylformamide was added with stirring. After stirring for 10 minutes, a solution (30 ml) of the compound (28 g, 78.4 mmol) synthesized in the above Step 6 in dimethylformamide was dropwise added. The mixture was warmed to room temperature and stirred for 60 hours. The mixture was neutralized with 1N hydrochloric acid and extracted twice with ethyl acetate (100 ml). The extracted organic layer was washed twice with water (100 ml) and dried over magnesium sulfate. The solvent was distilled away to give 24.1 g of the title compound as a colorless solid (yield 100%).

Step 8:

Synthesis of 4-[2-[2-(2-phenyl)-5-methyl-4-oxazolyl]ethoxy]benzyl alcohol

Sodium borohydride (2.46 g, 65.1 mmol) was gradually added to a solution (300 ml) of the compound (20 g, 65.1 mmol) synthesized in the above Step 7 in ethanol, and the mixture was stirred for 1 hour. Ethanol was distilled away and water (200 ml) was added. Filtration of the resulting precipitates gave 19.5 g of the title compound as a yellow solid (yield 97%).

Step 9:

Synthesis of 4-[2-[2-(2-phenyl)-5-methyl-4-oxazolyl]ethoxy]benzyl chloride

Thionyl chloride (8.9 ml, 124.2 mmol) was gradually added to a solution (300 ml) of the compound (19.18 g, 62.1 mmol) synthesized in the above Step 8 and zinc chloride (1.74 g, 12.78 mmol) in dioxane at room temperature, and the mixture was stirred for 1 hour. After stirring, dioxane and thionyl chloride were distilled away under reduced pressure and water (200 ml) was added. The mixture was extracted twice with dichloromethane (100 ml) and dried over magnesium sulfate. After drying, the solvent was distilled away to give 19.69 g of the title compound as a yellow solid (yield 94%).

Step 10:

Synthesis of diethyl 4-[2-[2-(2-phenyl)-5-methyl-4-oxazolyl]ethoxy]benzyl malonate A 60% oil of sodium hydride (488 mg, 12.2 mmol) was washed twice with n-hexane (5 ml) under a nitrogen stream and added with tetrahydrofuran (20 ml), and the mixture was cooled to 0° C. Diethyl malonate (1.95 g, 12.2 mmol) was added with stirring. After stirring for 30 minutes, the compound (4 g, 12.2 mmol) synthesized in the above Step 9 was added and the mixture was heated at 70° C. for 2 hours. The mixture was warmed to room temperature and the mixture was neutralized with 1N hydrochloric acid. The mixture was extracted twice with dichloromethane (100 ml) and dried over magnesium sulfate. The solution was purified by fast flow liquid chromatography (developing solvent; hexane:ethyl acetate=2:1) to give 3.13 g of the title compound as a colorless solid (yield 57%).

Step 11:

Synthesis of 4-[4-[2-(2-phenyl-5-methyl-4-oxazolyl)ethoxy]benzyl]-3,5-isoxazolidinedione A solution (4 ml) of hydroxyamine.hydrochloride (348 mg, 5.00 mmol) in anhydrous methanol was added to a solution (4 ml) of sodium methoxide (540 mg, 9.99 mmol) in anhydrous methanol at 0° C. The resulting sodium chloride was filtered off and a solution (4 ml) of the compound (1.5 g, 3.33 mol) synthesized in the above Step 10 in anhydrous methanol was added. The mixture was stirred overnight at room temperature. After stirring, the solvent was distilled away, and the residue was dissolved in an aqueous solution of sodium hydroxide and washed twice with ether (20 ml). 1N Hydrochloric acid was added to the aqueous layer to make same acidic. The mixture was extracted twice with ether (50 ml), dried over magnesium sulfate. The obtained solid was dissolved in ether and an insoluble material was removed. Evaporation of ether under reduced pressure gave 412 mg of the title compound as a colorless solid (yield 32%).

EXAMPLE 1'

Synthesis of dimethyl 4-[2-(2-phenyl-5-methyl-4-oxazolyl)ethoxy]benzilidene malonate (Step 18)

Dimethyl malonate (1.39 g, 0.01 mol), acetic acid (0.3 ml) and piperidine (0.3 ml) were added to a solution of the compound (2.94 g, 0.01 mol) synthesized in Example 1, Step 7 in toluene (30 ml), and the mixture was refluxed under heating using a Dean Stark trap while removing water to outside the system. Four hours later, toluene was distilled away and the obtained residue was recrystallized from methanol to give a colorless solid (2.5 g, yield 60%).

Synthesis of dimethyl 4-[2-[2-(2-phenyl)-5-methyl-4-oxazolyl]ethoxy]benzyl malonate
(Step 19)

The above-mentioned compound (2.5 g, 0.06 mol) was dissolved in a mixed solvent of methanol-dioxane (1:5, 20 ml), and 5% Pd—C (150 mg) was added. The mixture was vigorously stirred under an $H_2$ atmosphere at normal temperature and under atmospheric pressure. Two hours later, the catalyst was filtered off and the solvent was distilled away to give a solid. Recrystallization from methanol gave a colorless solid (2.15 g, yield 85%).

Synthesis of 4-[4-[2-(2-phenyl-5-methyl-4-oxazolyl)ethoxy]benzyl]-3,5-isoxazolidinedione
(Step 11)

A solution (4 ml) of sodium methoxide (574 mg, 10.6 mmol) in anhydrous methanol was gradually added to hydroxyamine.hydrochloride (360 mg, 5.3 mmol) in anhydrous methanol solvent (4 ml). The precipitated sodium chloride was filtered off, and a solution (4 ml) of the above-mentioned compound (1.5 g, 3.5 mmol) in anhydrous methanol was added. The mixture was stirred at 60° C. for 3 hours.

The solvent was distilled away, and 1N aqueous HCl (50 ml) was added to the residue to make same assume acidity. The residue was extracted twice with ether (50 ml) and dried over magnesium sulfate. The solvent was distilled away and the obtained solid was recrystallized twice from methanol to give 650 mg of a colorless solid (yield 47%).

mp: 154.6°–155.4° C.

The signals at 400 MHz NMR: 2.35 (s,3H), 2.92 (t,J=6.5 Hz,2H), 3.23–3.27 (m,2H), 3.50 (t,J=4.9 Hz,1H), 4.11 (t,J=6.7 Hz,2H), 6.77–7.95 (m,9H)

Reference Example 1

Synthesis of diethyl 4-hydroxybenzilidene malonate

4-Hydroxybenzaldehyde (24.4 g, 0.20 mol), diethyl malonate (30.4 ml, 0.2 mol), benzoic acid (3.0 g) and piperidine (3.0 ml) were dissolved in toluene (200 ml), and the mixture was refluxed for 6 hours with dehydration using a Dean Stark trap. After cooling the mixture to room temperature, the resulting solid was filtrated and washed with toluene, a 0.5N aqueous solution of citric acid, a saturated aqueous solution of sodium hydrogencarbonate and ether in order. The obtained solid was dried under reduced pressure to quantitatively give the title compound as a white solid.

EXAMPLE 2

Step 22:

Synthesis of diethyl 4-[2-(2-phenyl-5-methyl-4-oxazolyl)ethoxy]benzilidene malonate A 60% oil of sodium hydride (616 mg, 15.4 mmol) was washed twice with n-hexane (2 ml) under a nitrogen stream and added with dimethylformamide (20 ml). The mixture was cooled to 0° C. Diethyl 4-hydroxybenzilidene malonate (4.07 g, 15.4 mmol) synthesized in the above Reference Example 1 was added to this solution. After stirring for 10 minutes, the compound (5.00 g, 14.0 mmol) synthesized in Example 1, Step 6 was added and the mixture was stirred overnight. The reaction mixture was extracted with ethyl acetate, and the extract was washed with water and saturated brine. After the washing, the organic layer was dried over magnesium sulfate and the solvent was distilled away under reduced pressure. The obtained residue was purified by silica gel column chromatography (developing solvent; chloroform:methanol=98:2) to give 5.44 g of the title compound as a white solid.

Step 23:

Synthesis of 4-[4-[2-(2-phenyl-5-methyl-4-oxazolyl) ethoxy]benzilidene]-3,5-isoxazolidinedione A solution (10 ml) of hydroxyamine. hydrochloride (977 mg, 14.1 mmol) in anhydrous methanol was added to a solution (10 ml) of sodium methoxide (956 mg, 14.1 mmol) in anhydrous methanol at 0° C. The resulting sodium chloride was filtered off and a solution (10 ml) of the compound (4.21 g, 9.37 mol) synthesized in the above Step 17 in anhydrous methanol was added. An equivalent of sodium methoxide was added, and the mixture was stirred for 3 hours. After stirring, the solvent was distilled away, and the residue was extracted with ethyl acetate, washed with dilute hydrochloric acid and saturated brine, and dried over magnesium sulfate. The solvent was distilled away. The obtained solid was dissolved in ether and an insoluble material was removed. Ether was distilled away under reduced pressure, and the residue was purified by silica gel column chromatography (developing solvent; chloroform:methanol=95:5) to give 1.45 g of the title compound as a white solid (yield 32%).

EXAMPLES 3 AND 4

In the same manner as in Example 1, the compounds of Table 1 were obtained.

TABLE 1

| No. | Compound | Melting temp. | ¹H NMR (CDCl₃ δ value) |
|---|---|---|---|
| 1 | (structure: phenyl-C(=O)-oxazoline with N=C-Me, CH₂CH₂-O-C₆H₄-CH₂-CH(C(=O)Me)(C(=O)NH-O)) | 91.7–94.2° C. | 2.35(s, 3H), 2.92(t, J=6.5Hz, 2H), 3.01–3.70(m, 3H), 4.11(t, J=6.7Hz, 2H), 6.75–8.00(m, 9H) |
| 1' | (structure similar to 1) | 154.6–155.4° C. | 2.35(s, 3H), 2.92(t, J=6.5Hz, 2H), 3.23–3.27(m, 2H), 3.50(t, J=4.9Hz, 1H), 4.11(t, J=6.7Hz, 2H), 6.77–7.95(m, 9H) |
| 2 | (structure: phenyl variant with =CH exocyclic) | 151.2–152.4° C. | 2.37(s, 3H), 3.00(t, J=6.8Hz, 2H), 4.30(t, J=6.8Hz, 2H), 6.88(d, J=8.8Hz, 2H), 7.41(m, 5H), 7.92(brs, 1H), 7.98(m, 2H), 8.07(s, 1H) |
| 3 | (structure: benzothiophene variant) | 114.0–116.5 C. | 2.37(s, 3H), 2.94(t, J=6.4Hz, 2H), 3.19–3.51(m, 3H), 4.15(t, J=6.4Hz, 2H), 6.78(d, J=8.6Hz, 2H), 7.13(d, J=8.6Hz, 2H), 7.37(m, 2H), 7.82(m, 2H) |
| 4 | (structure: pyridylthio-CH(Me)- variant) | 100.0–102.0° C. | 1.68(t, J=7.1Hz, 3H), 2.21(s, 3H), 2.79(t, J=6.6Hz, 2H), 2.95(d, J=7.8Hz, 2H), 3.49(t, J=7.8Hz, 1H), 4.08(t, J=6.6Hz, 2H), 5.22(q, J=7.1Hz, 1H), 6.80(d, J=8.6Hz, 2H), 7.10(d, J=8.6Hz, 2H), 7.1–7.2(m, 1H), 7.32(m, 1H), 7.66(m, 1H), 8.46(m, 1H) (DMSO-d₆) |

As mentioned above, the present invention is not limited to the above-mentioned Examples. For example, the compounds shown in the following Tables 2 to 17 are also encompassed in the present invention.

TABLE 2

(General structure: R–C(=O)–oxazoline[R₅]=C–N–CH(R₄)–CH₂–O–C₆H₄–CH₂–CH(C(=O)Me)(C(=O)NH–O))

| R | R₄ | R₅ | R | R₄ | R₅ | R | R₄ | R₅ |
|---|---|---|---|---|---|---|---|---|
| HO–C₆H₄– | H | Me | cyclohexyl | H | Me | pyridyl | H | Me |
| Me–C₆H₄– | " | " | Me–cyclohexyl | " | " | HOOC–pyridyl | " | " |

TABLE 2-continued
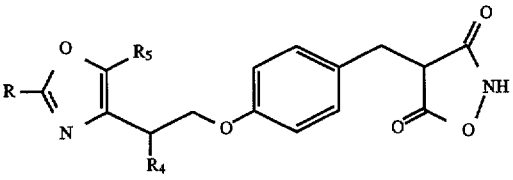
| R | R4 | R5 | R | R4 | R5 | R | R4 | R5 |
|---|---|---|---|---|---|---|---|---|
| 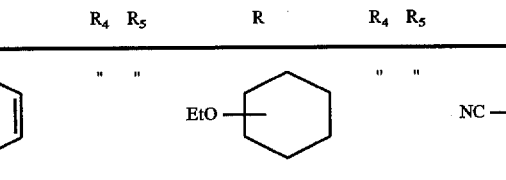 EtO, EtO | " | " | 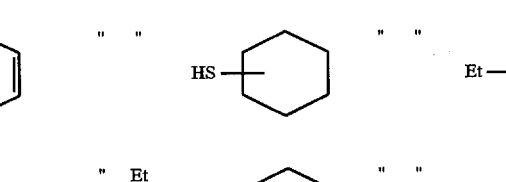 EtO | " | " | 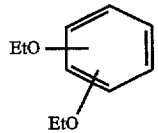 NC | " | Et |
| 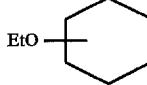 HS | " | " | 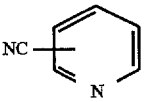 HS | " | " | 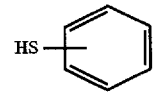 Et | " | " |
| 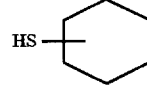 BnO | " | Et | 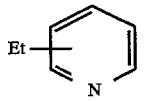 HO | " | " | 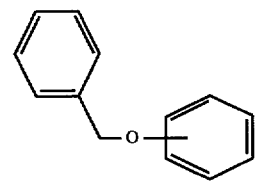 H2N | " | Me |
| 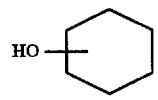 O2N | " | " | 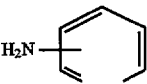 O2N | Et | " | 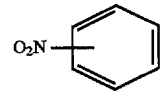 Me, Me | " | " |
| 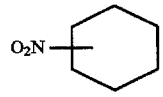 HOOC | " | " | 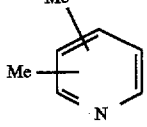 H3COOC | " | Et | 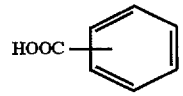 EtO | Me | " |
| 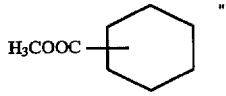 NC | " | " | 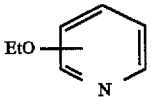 MeS | H | Me | 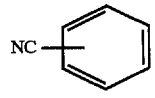 Br | H | " |
| 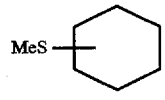 Cl | " | " | 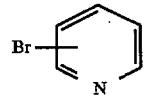 H2N | " | " | 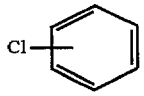 HO | " | " |
| 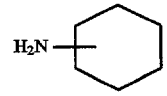 H2N | Me | " | 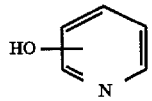 Br | " | " | 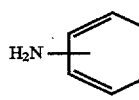 H2N | " | " |

TABLE 3

(structure: R-substituted oxazole with R5 on ring, linked via CH(R4)-CH2-O-phenyl-CH2-CH(COCH3)-C(=O)-NH-O ring)

| R | R4 | R5 | R | R4 | R5 | R | R4 | R5 |
|---|---|---|---|---|---|---|---|---|
| pyrimidinyl | H | Me | 5-Et-thienyl | H | Me | N-Me-imidazolyl | H | Me |
| 5-Bu-pyrimidinyl | " | " | 5-EtO-thienyl | " | " | 5-EtO-imidazolyl (NH) | " | " |
| 5-MeO-pyrimidinyl | " | Et | 5-EtS-thienyl | " | " | 5-HO-imidazolyl (NH) | " | Et |
| 5-HS-pyrimidinyl | " | Me | 5-HO-thienyl | " | " | 5-HS-imidazolyl (NH) | " | " |
| 5-HO-pyrimidinyl | " | " | 5-O2N-thienyl | " | " | 5-H2N-imidazolyl (NH) | " | Me |
| 5-O2N-pyrimidinyl | " | " | 5-H3COC-thienyl | Et | " | 5-O2N-imidazolyl (NH) | " | " |
| 5-HOOC-pyrimidinyl | " | " | 5-NC-thienyl | " | Et | 5-HOOC-imidazolyl (NH) | Me | " |
| 5-NC-pyrimidinyl | " | " | 5-H2N-thienyl | H | Me | 5-NC-imidazolyl (NH) | H | " |
| 5,6-di-Cl-pyrimidinyl | " | " | 5-Cl-thienyl | " | " | 5-Br-imidazolyl (NH) | " | " |

TABLE 3-continued
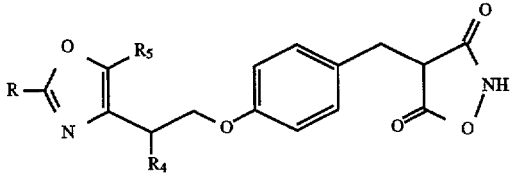
| R | R₄ | R₅ | R | R₄ | R₅ | R | R₄ | R₅ |
|---|---|---|---|---|---|---|---|---|
| 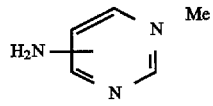 | Me | " | 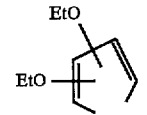 | " | " | 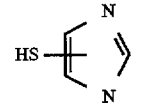 | " | " |
TABLE 4
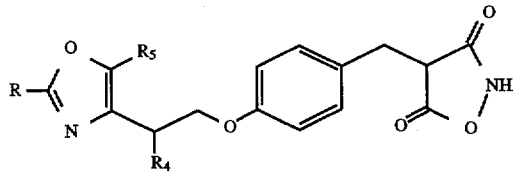
| R | R₄ | R₅ | R | R₄ | R₅ | R | R₄ | R₅ |
|---|---|---|---|---|---|---|---|---|
| 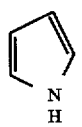 | H | Me | 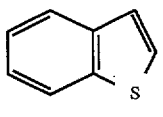 | H | Me | 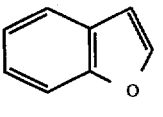 | H | Me |
| 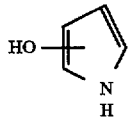 | " | " | 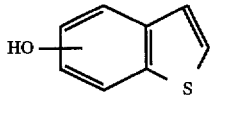 | " | " | 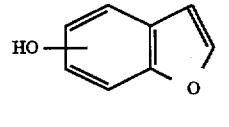 | " | " |
| 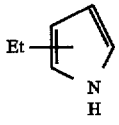 | " | Et | 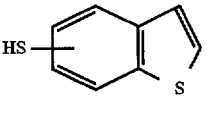 | " | " | 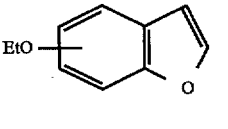 | " | Et |
| 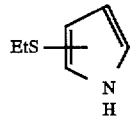 | " | Me | 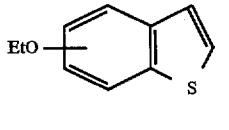 | " | " | 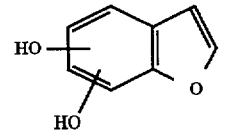 | " | " |
| 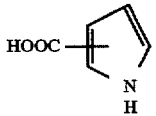 | " | " | 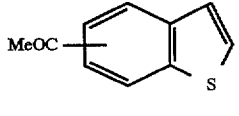 | " | " | 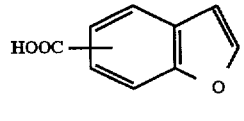 | " | Me |
| 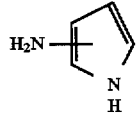 | " | " | 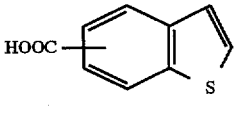 | Et | " | 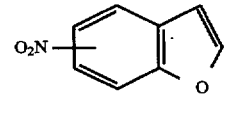 | " | " |

TABLE 4-continued

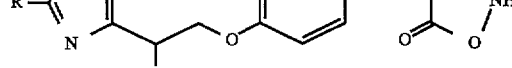

| R | R4 | R5 | R | R4 | R5 | R | R4 | R5 |
|---|---|---|---|---|---|---|---|---|
| O2N-[pyrrole-NH] | " | " | MeO-[benzothiophene]-MeO | " | Et | NC-[benzofuran] | Me | " |
| Cl-[pyrrole-NH] | " | " | H2N-[benzothiophene]-Cl | H | Me | H2N-[benzofuran] | H | " |
| Et2N-[pyrrole-NH] | " | " | Cl-[benzothiophene] | " | " | Cl-[benzofuran] | " | " |
| BuOC-[pyrrole-NH] | Me | " | t-Bu-[benzothiophene] | " | " | Me-[benzofuran] | " | " |

TABLE 5

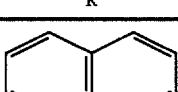

| R | R4 | R5 | R | R4 | R5 | R | R4 | R5 |
|---|---|---|---|---|---|---|---|---|
| [quinoline] | H | Me | [quinazoline] | H | Me | [chroman] | H | Me |
| HS-[quinoline] | " | " | HS-[quinazoline] | " | " | HO-[chroman] | " | " |
| BuO-[quinoline] | " | Et | BuO-[quinazoline] | " | " | MeO-[chroman] | " | Et |
| H2N-[quinoline] | " | Me | H2N-[quinazoline] | " | " | H2N-[chroman] | " | " |

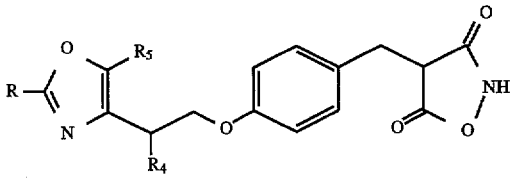

TABLE 6-continued
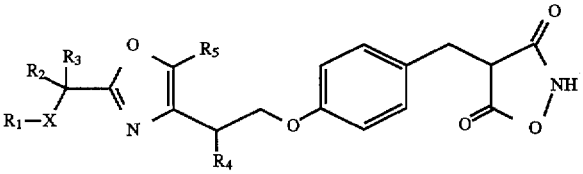
| R₁ | X | R₂ | R₃ | R₄ | R₅ | R₁ | X | R₂ | R₃ | R₄ | R₅ |
|---|---|---|---|---|---|---|---|---|---|---|---|
| 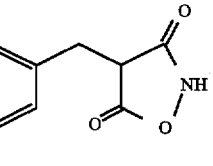 Me— | " | " | " | " | " | 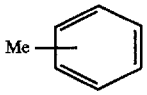 Et₂N— | " | " | H | " | Et |
| 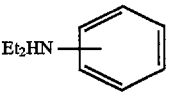 EtO— | " | " | H | Me | " | 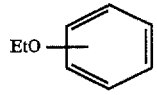 t-Bu—,t-Bu— | " | " | " | Et | " |
| 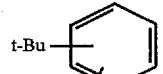 HS— | " | " | " | " | Et | 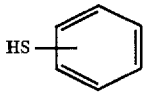 MeO—,MeO— | " | " | " | " | Me |
| 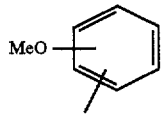 BnO— | " | " | " | H | Me | 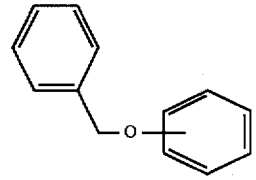 Cl—,Cl— | " | " | " | " | " |
| 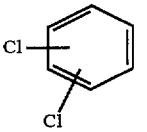 O₂N— | " | " | " | " | " | 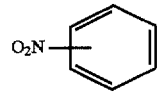 H₂N—,Cl— | " | " | " | H | " |
| 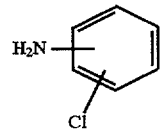 HOOC— | " | " | Me | " | " | 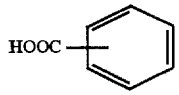 t-Bu—,HO—,t-Bu— | " | " | Me | " | " |
| 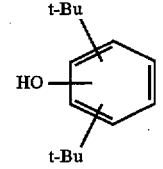 NC— | " | " | " | " | " | 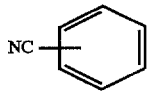 H₂N—,HO— | " | " | " | " | " |
| 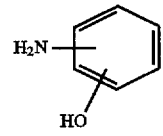 Cl— | " | " | " | " | " | 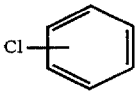 Me—,Cl— | " | " | " | " | " |

TABLE 7
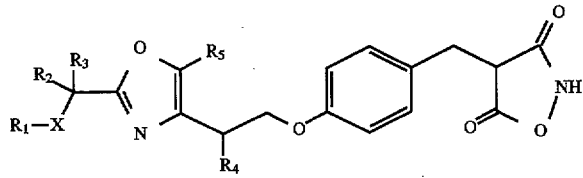
| R₁ | X | R₂ | R₃ | R₄ | R₅ | R₁ | X | R₂ | R₃ | R₄ | R₅ |
|---|---|---|---|---|---|---|---|---|---|---|---|
| 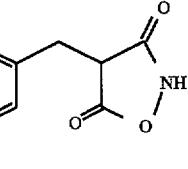 | S | H | Me | H | Me | 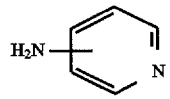 | S | H | Me | H | Me |
| 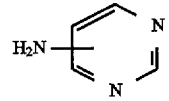 | " | " | " | " | " | 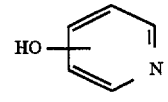 | " | " | " | " | " |
| 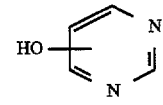 | " | " | " | " | " | 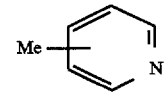 | " | " | H | " | Et |
| 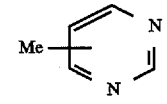 | " | " | H | Me | " | 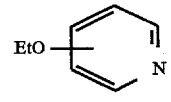 | " | " | " | Et | " |
| 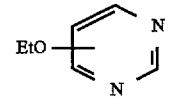 | " | " | " | " | Et | 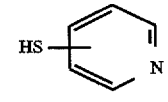 | " | " | " | " | Me |
| 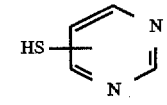 | " | " | " | H | Me | 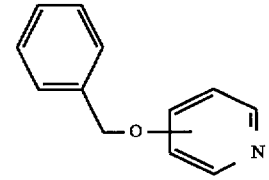 | " | " | " | " | " |
| 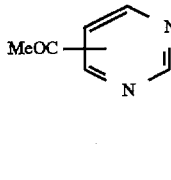 | " | " | " | " | " | 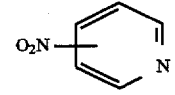 | " | " | " | H | " |
| 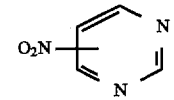 | " | " | Me | " | " | 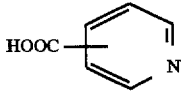 | " | " | Me | " | " |
| 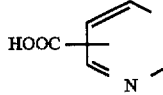 | " | " | " | " | " | 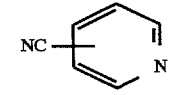 | " | " | " | " | " |
| 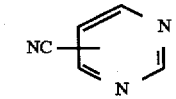 | " | " | " | " | " | 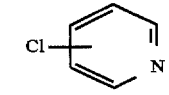 | " | " | " | " | " |

TABLE 8

| R₁ | X | R₂ | R₃ | R₄ | R₅ | R₁ | X | R₂ | R₃ | R₄ | R₅ |
|---|---|---|---|---|---|---|---|---|---|---|---|
| H₂N–cyclohexyl– | S | H | Me | H | Me | imidazol-1-yl– | S | H | Me | H | Me |
| HO–cyclohexyl– | " | " | " | " | " | HO–(imidazol-NH)– | " | " | " | " | " |
| Me–cyclohexyl– | " | " | " | " | " | H₂N–(imidazol-NH)– | " | " | H | " | Et |
| EtO–cyclohexyl– | " | " | H | Me | " | Et–(imidazol-NH)– | " | " | " | Et | " |
| HS–cyclohexyl– | " | " | " | " | Et | EtO–(imidazol-NH)– | " | " | " | " | Me |
| H₂NOC–cyclohexyl– | " | " | " | H | Me | HS–(imidazol-NH)– | " | " | " | " | " |
| O₂N–cyclohexyl– | " | " | " | " | " | NC–(imidazol-NH)– | " | " | " | H | " |
| HOOC–cyclohexyl– | " | " | Me | " | " | O₂N–(imidazol-NH)– | " | " | Me | " | " |
| NC–cyclohexyl– | " | " | " | " | " | HOOC–(imidazol-NH)– | " | " | " | " | " |

TABLE 8-continued
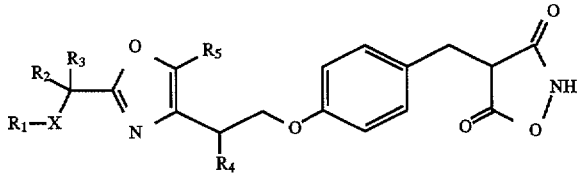
| R₁ | X | R₂ | R₃ | R₄ | R₅ | R₁ | X | R₂ | R₃ | R₄ | R₅ |
|---|---|---|---|---|---|---|---|---|---|---|---|
| 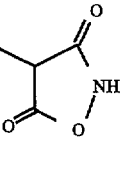 | " | " | " | " | " | 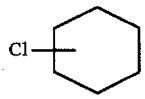 | " | " | " | " | " |
TABLE 9
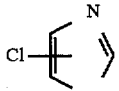
| R₁ | X | R₂ | R₃ | R₄ | R₅ | R₁ | X | R₂ | R₃ | R₄ | R₅ |
|---|---|---|---|---|---|---|---|---|---|---|---|
| 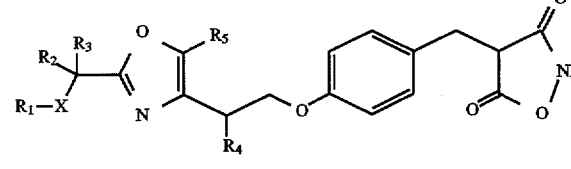 | S | H | Me | H | Me | 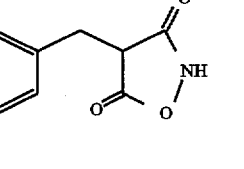 | S | H | Me | H | Me |
| 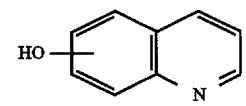 | " | " | " | " | " | 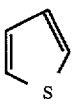 | " | " | " | " | " |
| 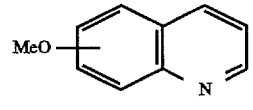 | " | " | " | " | " | 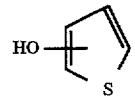 | " | " | H | " | Et |
| 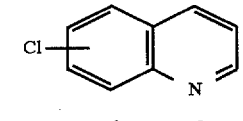 | " | " | H | Me | " | 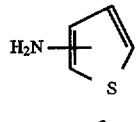 | " | " | " | Et | " |
| 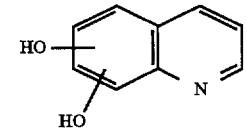 | " | " | " | " | Et | 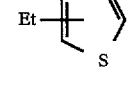 | " | " | " | " | Me |
| 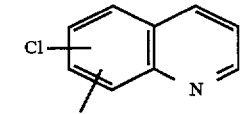 | " | " | " | H | Me | 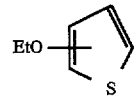 | " | " | " | " | " |
| 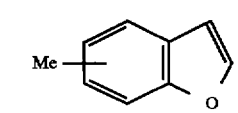 | " | " | " | " | " | 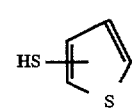 | " | " | " | H | " |
| 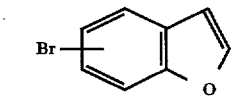 | " | " | Me | " | " | 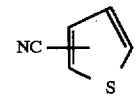 | " | " | Me | " | " |

TABLE 9-continued
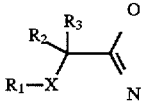
| $R_1$ | X | $R_2$ | $R_3$ | $R_4$ | $R_5$ | $R_1$ | X | $R_2$ | $R_3$ | $R_4$ | $R_5$ |
|---|---|---|---|---|---|---|---|---|---|---|---|
| 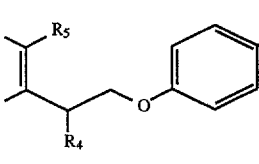 | " | " | " | " | " | 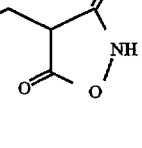 | " | " | " | " | " |
|  | " | " | " | " | " | 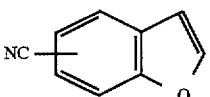 | " | " | " | " | " |
TABLE 10
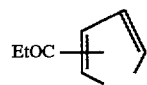
| $R_1$ | X | $R_2$ | $R_3$ | $R_4$ | $R_5$ | $R_1$ | X | $R_2$ | $R_3$ | $R_4$ | $R_5$ |
|---|---|---|---|---|---|---|---|---|---|---|---|
| 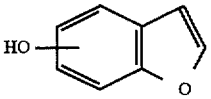 | O | H | Me | H | Me | 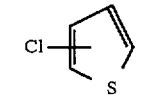 | O | H | Me | H | Me |
| 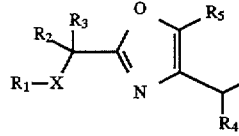 | " | " | " | " | " | 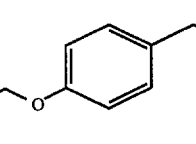 | " | " | " | " | " |
| 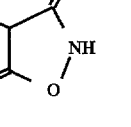 | " | " | " | " | " |  | " | " | H | " | Et |
|  | " | " | H | Me | " | 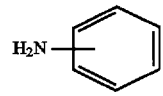 | " | " | " | Et | " |
| 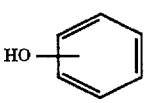 | " | " | " | " | Et | 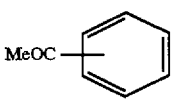 | " | " | " | " | Me |
| 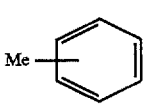 | " | " | " | H | Me | 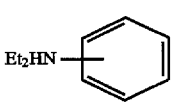 | " | " | " | " | " |

TABLE 10-continued

| R₁ | X | R₂ | R₃ | R₄ | R₅ | R₁ | X | R₂ | R₃ | R₄ | R₅ |
|---|---|---|---|---|---|---|---|---|---|---|---|
| O₂N–C₆H₄– | " | " | " | " | " | H₂N–C₆H₃(Cl)– | " | " | " | H | " |
| HOOC–C₆H₄– | " | " | Me | " | " | t-Bu,HO,t-Bu–C₆H₂– | " | " | Me | " | " |
| NC–C₆H₄– | " | " | " | " | " | H₂N,HO–C₆H₃– | " | " | " | " | " |
| Cl–C₆H₄– | " | " | " | " | " | Me,Cl–C₆H₃– | " | " | " | " | " |

TABLE 11

| R₁ | X | R₂ | R₃ | R₄ | R₅ | R₁ | X | R₂ | R₃ | R₄ | R₅ |
|---|---|---|---|---|---|---|---|---|---|---|---|
| H₂N-pyridyl | O | H | Me | H | Me | H₂N-pyrimidinyl | O | H | Me | H | Me |
| HO-pyridyl | " | " | " | " | " | HO-pyrimidinyl | " | " | " | " | " |
| Me-pyridyl | " | " | " | " | " | Me-pyrimidinyl | " | " | H | " | Et |
| EtO-pyridyl | " | " | H | Me | " | EtO-pyrimidinyl | " | " | " | Et | " |

TABLE 11-continued
| R₁ | X | R₂ | R₃ | R₄ | R₅ | R₁ | X | R₂ | R₃ | R₄ | R₅ |
|---|---|---|---|---|---|---|---|---|---|---|---|
| HS-pyridyl | " | " | " | " | Et | HS-pyrimidyl | " | " | " | " | Me |
| BnO-pyridyl | " | " | " | H | Me | MeOC-pyrimidyl | " | " | " | " | " |
| O₂N-pyridyl | " | " | " | " | " | O₂N-pyrimidyl | " | " | " | " | H | " |
| HOOC-pyridyl | " | " | Me | " | " | HOOC-pyrimidyl | " | " | Me | " | " |
| NC-pyridyl | " | " | " | " | " | NC-pyrimidyl | " | " | " | " | " |
| Cl-pyridyl | " | " | " | " | " | Cl-pyrimidyl | " | " | " | " | " |
TABLE 12
| R₁ | X | R₂ | R₃ | R₄ | R₅ | R₁ | X | R₂ | R₃ | R₄ | R₅ |
|---|---|---|---|---|---|---|---|---|---|---|---|
| H₂N-cyclohexyl | O | H | Me | H | Me | imidazolyl | O | H | Me | H | Me |

TABLE 12-continued
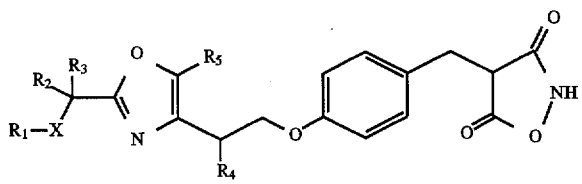
| R₁ | X | R₂ | R₃ | R₄ | R₅ | R₁ | X | R₂ | R₃ | R₄ | R₅ |
|---|---|---|---|---|---|---|---|---|---|---|---|
| 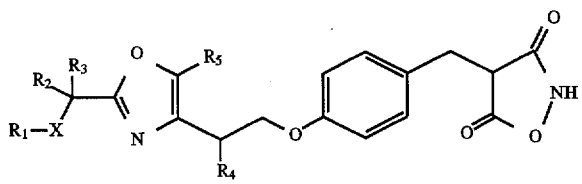 HO— | " | " | " | " | " | 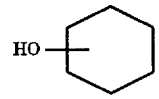 HO— | " | " | " | " | " |
| 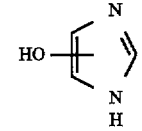 Me— | " | " | " | " | " | 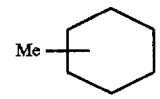 H₂N— | " | " | H | " | Et |
| 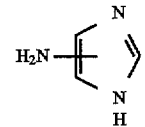 EtO— | " | " | H | Me | " | 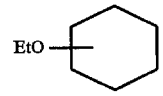 Et— | " | " | " | Et | " |
| 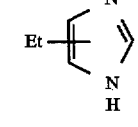 HS— | " | " | " | " | Et | 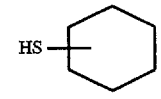 EtO— | " | " | " | " | Me |
| 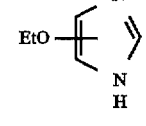 H₂NOC— | " | " | " | H | Me | 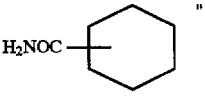 HS— | " | " | " | " | " |
| 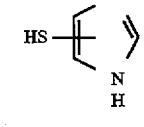 O₂N— | " | " | " | " | " | 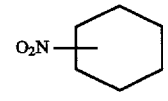 NC— | " | " | " | H | " |
| 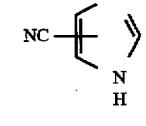 HOOC— | " | " | Me | " | " | 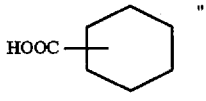 O₂N— | " | " | Me | " | " |
| 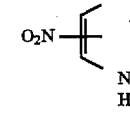 NC— | " | " | " | " | " | 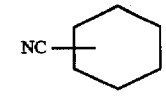 HOOC— | " | " | " | " | " |
| 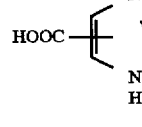 Cl— | " | " | " | " | " | 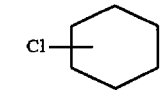 Cl— | " | " | " | " | " |

TABLE 13
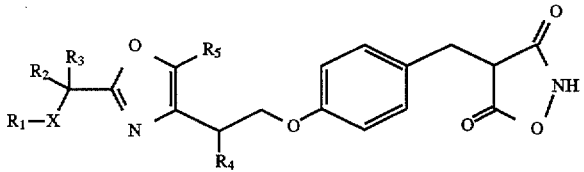
| $R_1$ | X | $R_2$ | $R_3$ | $R_4$ | $R_5$ | $R_1$ | X | $R_2$ | $R_3$ | $R_4$ | $R_5$ |
|---|---|---|---|---|---|---|---|---|---|---|---|
| 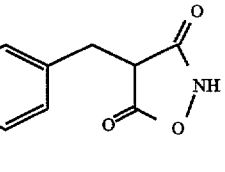 | O | H | Me | H | Me | 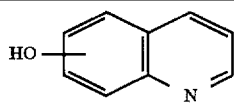 | O | H | Me | H | Me |
| 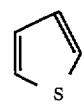 | " | " | " | " | " | 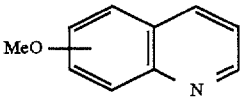 | " | " | " | " | " |
| 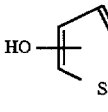 | " | " | " | " | " | 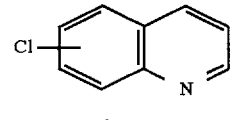 | " | " | H | " | Et |
| 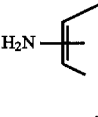 | " | " | H | Me | " | 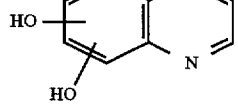 | " | " | " | Et | " |
| 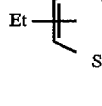 | " | " | " | " | Et | 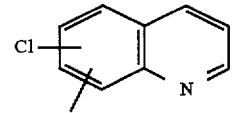 | " | " | " | " | Me |
| 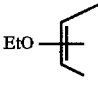 | " | " | " | H | Me | 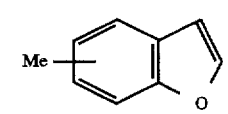 | " | " | " | " | " |
| 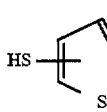 | " | " | " | " | " | 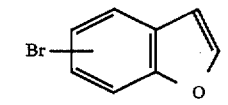 | " | " | " | H | " |
| 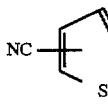 | " | " | Me | " | " | 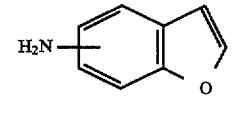 | " | " | Me | " | " |
| 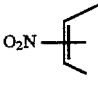 | " | " | " | " | " | 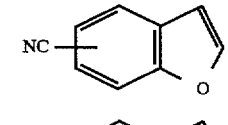 | " | " | " | " | " |
| 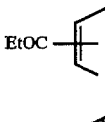 | " | " | " | " | " | 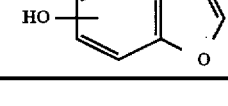 | " | " | " | " | " |

TABLE 14
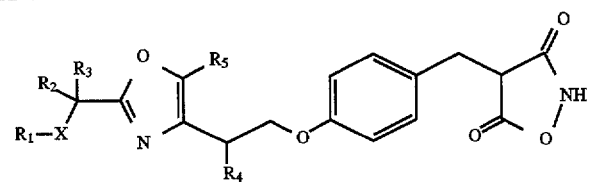
| $R_1$ | X | $R_2$ | $R_3$ | $R_4$ | $R_5$ | $R_1$ | X | $R_2$ | $R_3$ | $R_4$ | $R_5$ |
|---|---|---|---|---|---|---|---|---|---|---|---|
|  | NH | H | Me | H | Me |  | NH | H | Me | H | Me |
| 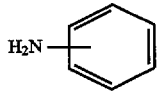 | " | " | " | " | " | 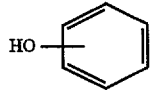 | " | " | " | " | " |
| 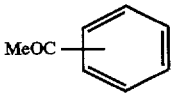 | " | " | " | " | " | 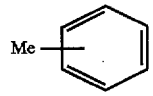 | " | H | " | Et |
| 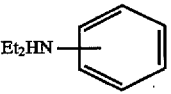 | " | " | H | Me | " | 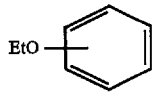 | " | " | " | Et | " |
| 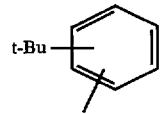 | " | " | " | " | Et | 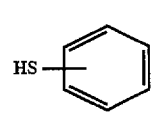 | " | " | " | " | Me |
| 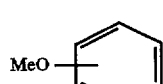 | " | " | " | H | Me | 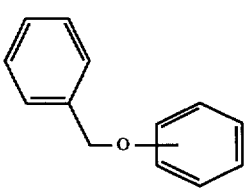 | " | " | " | " | " |
| 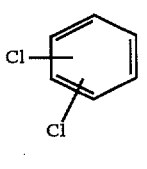 | " | " | " | " | " | 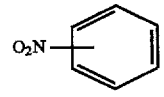 | " | " | " | H | " |
| 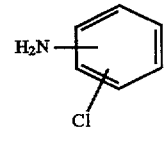 | " | " | Me | " | " | 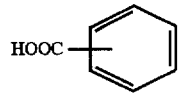 | " | " | Me | " | " |
| 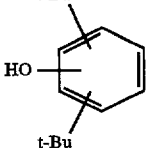 | " | " | " | " | " | 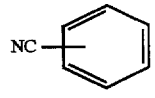 | " | " | " | " | " |

TABLE 14-continued

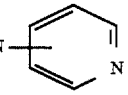

| R₁ | X | R₂ | R₃ | R₄ | R₅ | R₁ | X | R₂ | R₃ | R₄ | R₅ |
|---|---|---|---|---|---|---|---|---|---|---|---|
| 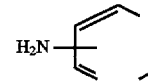 | " | " | " | " | " | 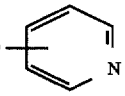 | " | " | " | " | " |

TABLE 15

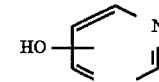

| R₁ | X | R₂ | R₃ | R₄ | R₅ | R₁ | X | R₂ | R₃ | R₄ | R₅ |
|---|---|---|---|---|---|---|---|---|---|---|---|
| 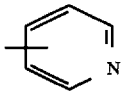 H₂N-pyridine | NH | H | Me | H | Me | 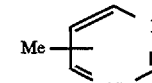 H₂N-pyrimidine | NH | H | Me | H | Me |
| 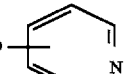 HO-pyridine | " | " | " | " | " | HO-pyrimidine | " | " | " | " | " |
| 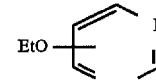 Me-pyridine | " | " | " | " | " | Me-pyrimidine | " | " | H | " | Et |
| 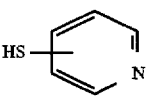 EtO-pyridine | " | " | H | Me | " | EtO-pyrimidine | " | " | " | Et | " |
| 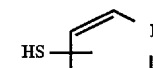 HS-pyridine | " | " | " | " | Et | HS-pyrimidine | " | " | " | " | Me |
|  BnO-pyridine | " | " | " | H | Me | MeOC-pyrimidine | " | " | " | " | " |
| 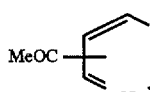 O₂N-pyridine | " | " | " | " | " | 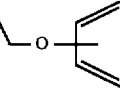 O₂N-pyrimidine | " | " | " | H | " |

TABLE 15-continued

| R₁ | X | R₂ | R₃ | R₄ | R₅ | R₁ | X | R₂ | R₃ | R₄ | R₅ |
|---|---|---|---|---|---|---|---|---|---|---|---|
| HOOC-pyridine | " | " | Me | " | " | HOOC-pyrimidine | " | " | Me | " | " |
| NC-pyridine | " | " | " | " | " | NC-pyrimidine | " | " | " | " | " |
| Cl-pyridine | " | " | " | " | " | Cl-pyrimidine | " | " | " | " | " |

TABLE 16

| R₁ | X | R₂ | R₃ | R₄ | R₅ | R₁ | X | R₂ | R₃ | R₄ | R₅ |
|---|---|---|---|---|---|---|---|---|---|---|---|
| H₂N-cyclohexyl | NH | H | Me | H | Me | imidazole (N-linked) | NH | H | Me | H | Me |
| HO-cyclohexyl | " | " | " | " | " | HO-pyrrole(NH) | " | " | " | " | " |
| Me-cyclohexyl | " | " | " | " | " | H₂N-pyrrole(NH) | " | " | H | " | Et |
| EtO-cyclohexyl | " | " | H | Me | " | Et-pyrrole(NH) | " | " | " | " | Et | " |

TABLE 16-continued
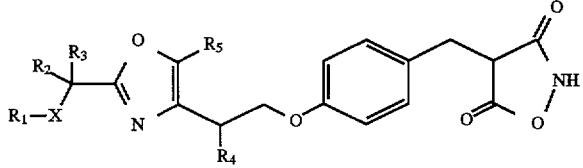
| R₁ | X | R₂ | R₃ | R₄ | R₅ | R₁ | X | R₂ | R₃ | R₄ | R₅ |
|---|---|---|---|---|---|---|---|---|---|---|---|
| 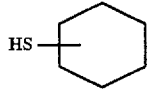 | " | " | " | " | Et | 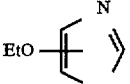 | " | " | " | " | Me |
| 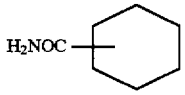 | " | " | " | H | Me | 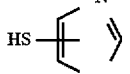 | " | " | " | " | " |
| 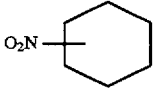 | " | " | " | " | " | 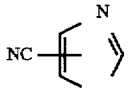 | " | " | " | H | " |
| 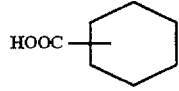 | " | " | Me | " | " | 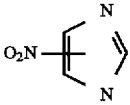 | " | " | Me | " | " |
| 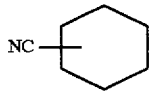 | " | " | " | " | " | 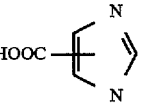 | " | " | " | " | " |
| 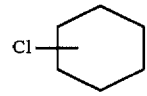 | " | " | " | " | " | 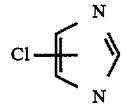 | " | " | " | " | " |
TABLE 17
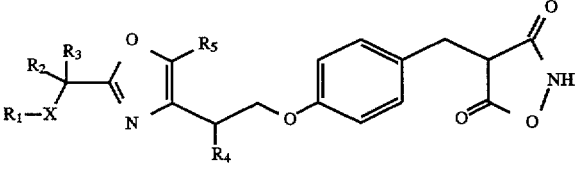
| R₁ | X | R₂ | R₃ | R₄ | R₅ | R₁ | X | R₂ | R₃ | R₄ | R₅ |
|---|---|---|---|---|---|---|---|---|---|---|---|
| 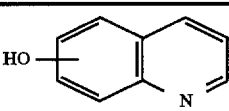 | NH | H | Me | H | Me | 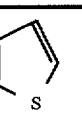 | NH | H | Me | H | Me |
| 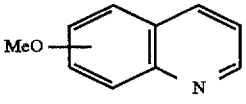 | " | " | " | " | " | 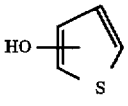 | " | " | " | " | " |

TABLE 17-continued

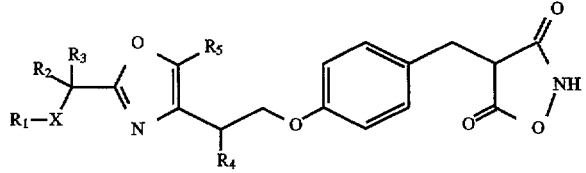

| R₁ | X | R₂ | R₃ | R₄ | R₅ | R₁ | X | R₂ | R₃ | R₄ | R₅ |
|---|---|---|---|---|---|---|---|---|---|---|---|
| 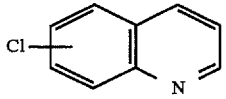 | " | " | " | " | " | 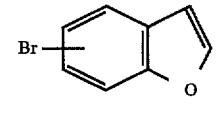 | " | " | H | " | Et |
| 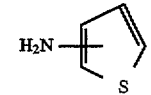 | " | " | H | Me | " | 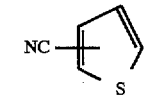 | " | " | " | Et | " |
| 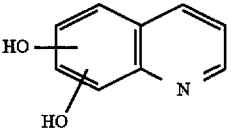 | " | " | " | " | Et | 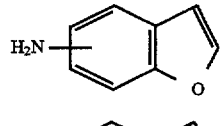 | " | " | " | " | Me |
| 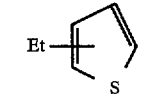 | " | " | " | H | Me | 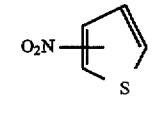 | " | " | " | " | " |
| 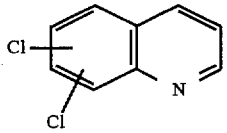 | " | " | " | " | " | 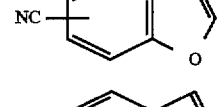 | " | " | " | H | " |
| 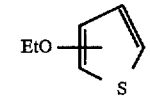 | " | " | Me | " | " | 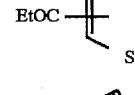 | " | " | Me | " | " |
| 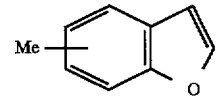 | " | " | " | " | " | 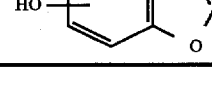 | " | " | " | " | " |
| 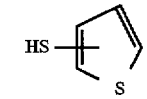 | " | " | " | " | " | 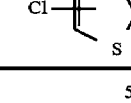 | " | " | " | " | " |

Experimental Example 1

Genetically obese, hyperglycemic and hyperlipidemic diabetic mice (C57BL/Ksj-db/db, male, Jackson Laboratories/Clea Japan, Inc., 13 weeks of age and KK-Ay, male, Clea Japan, Inc., 13 weeks of age) were used for the pharmacological tests. As a reference compound, a hypoglycemic agent CS-045 [(±)-5-[4-(6-hydroxy-2,5,7,8-tetramethylchroman-2-yl-methoxy)benzyl]-2,4-thiazolidinedione] [see Diabetes, vol. 37, p. 1549 (1988)] was used.

The mice were weighed and blood samples were taken immediately before the initiation of administration on day 1. Serum glucose and serum triglyceride were measured, based on which the mice were grouped (6–8 per group) in such a manner that there existed no difference in terms of average body weight, average serum glucose and average serum triglyceride.

The test drugs were all suspended in a solution of 0.5% sodium carboxymethylcellulose and administered orally twice a day (the second administration was 6 hours after the first administration) on day 1, day 2, day 3 and day 4. To a vehicle control group, a solution of 0.5% sodium carboxymethylcellulose was orally administered.

At day 5, blood samples were taken again and measured for serum glucose and serum triglyceride. The blood sample was taken from orbital cavity plexus by 400 μl under anesthetization with ether and kept at ice temperature. After separation into serum (12000 rpm, 5 min.), serum glucose was measured by hexokinase method (glucose-HK-test "BMY"; Bohelinger Mannheim Yamanouchi) and serum triglyceride was measured by enzyme method (triglycolor III "BMY"; Bohelinger Mannheim Yamanouchi) using an automatic analyzer COBAS FARA (manufactured by Roche).

Change in percent of serum glucose and serum triglyceride in each group was calculated using serum glucose and serum triglyceride, respectively, of vehicle control group at day 5 as follows:

Change in percent of serum glucose (%) =

$$\left[\frac{\left(\begin{array}{c}\text{serum glucose of each}\\\text{group at day 5}\end{array}\right) - \left(\begin{array}{c}\text{serum glucose of vehicle}\\\text{control group at day 5}\end{array}\right)}{\text{serum glucose of vehicle control group at day 5}}\right] \times 100$$

Change in percent of serum triglyceride value (%) =

$$\left[\frac{\left(\begin{array}{c}\text{serum triglyceride of}\\\text{each group at day 5}\end{array}\right) - \left(\begin{array}{c}\text{serum triglyceride of vehicle}\\\text{control group at day 5}\end{array}\right)}{\text{serum triglyceride of vehicle control group at day 5}}\right] \times 100$$

The results are shown in Table 18.

TABLE 18

|  | dose (mg/kg) | serum glucose (%) | | serum triglyceride (%) | |
| --- | --- | --- | --- | --- | --- |
|  |  | KK-Aγ mouse | db/db mouse | KK-Aγ mouse | db/db mouse |
| Ex. 1 | 10 | −38.3 | −19.8 | −50.3 | −29.1 |
| CS-045 | 100 | −29.4 | −21.5 | −22.9 | −55.5 |

As shown in Table 18, the compound of the present invention lowered serum glucose and serum triglyceride of both kinds of diabetic mice more significantly than did the control compound.

From the foregoing, it is evident that the compound of the present invention has superior hypoglycemic and hypolipidemic actions and is useful for the treatment of diabetes and hyperlipidemia. In addition, the compound of the invention is expected to be efficacious for the prevention and treatment of the complications of diabetes.

Industrial Applicability

The isoxazolidine derivative compound (I) and a salt thereof of the present invention are novel compounds having extremely potent and low toxic hypoglycemic action as compared with known oxazolidine derivatives and other therapeutic agents of diabetes, and are very useful as therapeutic agents for diabetes and hyperlipidemia. In addition, the compounds of the present invention are expected to be useful for the prevention of the complications of diabetes, especially for the prevention of arteriosclerosis.

What is claimed is:

1. An isoxazolidinedione compound of the formula I

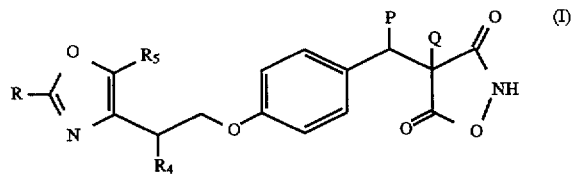

wherein

R is a phenyl, biphenyl or naphthyl, which is optionally substituted by 1 to 3 substituents; an alicyclic hydrocarbon having 3 to 7 carbon atoms, which is optionally substituted by 1 to 3 substituents; an oxazolyl, isoxazolyl or 5-membered heterocyclic group having 1 to 3 nitrogen atoms or 1 oxygen atom or 1 sulfur atom, which is optionally substituted by 1 to 3 substituents; a 5-membered heterocyclic group having 1 to 3 nitrogen atoms or 1 oxygen atom or 1 sulfur atom which is condensed with a phenyl; or a group of the formula

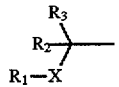

wherein $R_1$ is phenyl, biphenyl or naphthyl, which is optionally substituted by 1 to 3 substituents, an alicyclic hydrocarbon having 3 to 7 carbon atoms, which is optionally substituted by 1 to 3 substituents, an oxazolyl, isoxazolyl or 5-membered heterocyclic group having 1 to 3 nitrogen atoms, which is optionally substituted by 1 to 3 substituents, or a heterocyclic group which is condensed with a phenyl; $R_2$ and $R_3$ are the same or different and each is a hydrogen atom or a lower alkyl having 1 to 4 carbon atoms, and X is an oxygen atom; a sulfur atom or a secondary amino;

$R_4$ is a hydrogen atom or a lower alkyl having 1 to 4 carbon atoms;

$R_5$ is a lower alkyl having 1 to 4 carbon atoms; and

P and Q are each a hydrogen atom or P and Q together form a bond, said substituents being a group selected from hydroxyl, a lower alkyl having 1 to 4 carbon atoms and a lower alkoxyl having 1 to 4 carbon atoms;

or a pharmaceutically acceptable salt thereof.

2. The isoxazolidinedione compound of claim 1, wherein $R_4$ is a hydrogen atom and $R_5$ is a lower alkyl having 1 to 4 carbon atoms, or a pharmaceutically acceptable salt thereof.

3. The isoxazolidinedione compound of claim 2, wherein R is a phenyl optionally substituted by 1 to 3 substituents selected from hydroxyl, a lower alkyl having 1 to 4 carbon atoms and a lower alkoxyl having 1 to 4 carbon atoms.

4. The isoxazolidinedione compound of claim 3, wherein R is phenyl, or a pharmaceutically acceptable salt thereof.

5. The isoxazolidinedione compound of claim 2, wherein R is a group of the formula

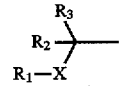

or a pharmaceutically acceptable salt thereof.

6. The isoxazolidinedione compound of claim 5, wherein $R_1$ is a phenyl optionally substituted by 1 to 3 substituents selected from hydroxyl, a lower alkyl having 1 to 4 carbon atoms and a lower alkoxyl having 1 to 4 carbon atoms, or a pharmaceutically acceptable salt thereof.

7. The isoxazolidinedione compound of claim 1, which is 4-[4-[2-(2-phenyl-5-methyl-4-oxazolyl)ethoxy]benzyl]-3,5-isoxazolidinedione, or 4-[4-[2-(2-phenyl-5-methyl-4-oxazolyl)ethoxy]benzylidene]-3,5-isoxazolidinedione, or a pharmaceutically acceptable salt thereof.

8. A pharmaceutical composition comprising the isoxazolidinedione compound of claim 1 or a pharmaceutically acceptable salt thereof in an effective amount, and a carrier.

9. A method for the treatment of diabetes in a human, comprising administering to the human an effective amount of the isoxazolidinedione compound of claim 1 or a pharmaceutically acceptable salt thereof.

10. A method for the treatment of hyperlipidemia in a human, comprising administering to the human an effective amount of the isoxazolidinedione compound of claim 1 or a pharmaceutically acceptable salt thereof.

* * * * *